United States Patent [19]

Zubovics et al.

[11] Patent Number: 4,922,021

[45] Date of Patent: May 1, 1990

[54] NEW ALKYLENE DIAMINE DERIVATIVES

[75] Inventors: Zoltan Zubovics; Lajos Toldy; Gyorgy Rabloczky; Andras Varro; Ferene Andrasi; Sandor Elek; Istvan Elekes, all of Budapest, Hungary

[73] Assignee: BASF Aktiensellschaft, Ludwigshafen, Fed. Rep. of Germany

[21] Appl. No.: 246,028

[22] Filed: Sep. 14, 1988

Related U.S. Application Data

[63] Continuation of Ser. No. 772,199, Sep. 4, 1985.

[30] Foreign Application Priority Data

Mar. 4, 1981 [HU] Hungary .................... 539/81

[51] Int. Cl.$^5$ ............... A61K 31/135; C07C 87/28
[52] U.S. Cl. .................... 564/367; 514/821; 564/304
[58] Field of Search ............ 564/367, 369, 354; 514/649, 821

[56] References Cited

U.S. PATENT DOCUMENTS

| | | | |
|---|---|---|---|
| 3,068,235 | 12/1962 | Shapiro et al. | 546/229 |
| 3,200,151 | 8/1965 | Spickett et al. | 564/367 X |
| 3,205,136 | 9/1965 | Tedeschi | 564/353 X |
| 3,328,249 | 6/1967 | Aceto | 564/374 X |
| 3,923,813 | 12/1975 | Vanhoof et al. | 564/367 X |
| 3,954,872 | 5/1976 | Koppe et al. | 564/353 |
| 3,981,872 | 9/1976 | Vanhoof et al. | 564/367 X |
| 4,286,983 | 9/1981 | Gilse et al. | 564/368 X |
| 4,322,434 | 3/1982 | Nenstadt et al. | 564/368 X |

FOREIGN PATENT DOCUMENTS

| | | | |
|---|---|---|---|
| 547301 | 8/1942 | United Kingdom | 564/367 |
| 604363 | 7/1948 | United Kingdom | 564/367 |

OTHER PUBLICATIONS

Wolff, "Burger's Medicinal Chemistry", Part III, pp. 84–87(1979).

Burger, "Medicinal Chemistry", 3rd Ed., Part II, pp. 1082–1085(1970).

Barron et al., "Jour. Med. Chemistry", vol. 6, pp. 705–711(1963).

Lazizza et al., "Gozz. Chim. Ital.", vol. 89, pp. 2018–2026(1959).

Primary Examiner—Robert V. Hines
Attorney, Agent, or Firm—Keil & Weinkauf

[57] ABSTRACT

The invention is directed to 1-(2,6-Dimethyl-Phenylamino)-2-Dimethyl-amino-Propane and the pharmaceutical composition thereof useful for the treatment of cardiac rhythm disorders.

2 Claims, No Drawings

NEW ALKYLENE DIAMINE DERIVATIVES

This is a continuation of Ser. No. 772,199, filed 9/4/85.

The invention relates to new alkylenediamine derivatives and pharmaceutical compositions containing the same, as well as to a process for the preparation thereof.

The new alkylenediamine derivatives of the invention correspond to the general formula (I),

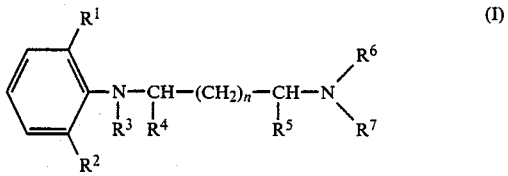

wherein
$R^1$ and $R^2$ each represent halogen or a lower alkyl group, $R^3$ stands for hydrogen, a lower alkyl group, an acyl group derived from a lower aliphatic carboxylic acid bearing optionally 1-3 halogen substituents or from an aromatic carboxylic acid, a lower alkoxycarbonyl group, or a sulfonyl group derived from a lower aliphatic sulfonic acid or an aromatic sulfonic acid, $R^4$ and $R^5$ each represent hydrogen or a lower alkyl group, $R^6$ and $R^7$ each represent hydrogen, a lower alkyl group bearing optionally a hydroxy or halogen substituent, an acyl group derived from a lower aliphatic carboxylic acid bearing optionally an amino or a mono- or di- (lower alkyl)-amino substituent, a lower alkoxy-carbonyl group, or a sulfonyl group derived from a lower aliphatic sulfonic acid or an aromatic sulfonic acid, or $R^6$ and $R^7$ may form, together with the adjacent nitrogen atom, a 3-7 membered heterocyclic group optionally containing a further hetero atom, such as an oxygen, sulfur or nitrogen atom, or a group derived from a cyclic imide of a dicarboxylic acid, and n is zero or one,
with the provisos that
(i) if $R^1$ and $R^2$ each stand for methyl group, at least one of $R^4$ and $R^5$ must be other than hydrogen, and
(ii) if $R^1$ and $R^2$ each stand for methyl group, $R^3$ and $R^5$ each stand for hydrogen, $R^4$ represents methyl or ethyl group and n is zero, at least one of $R^6$ and $R^7$ must be other than ethyl group.

Mixtures of the above compounds, optically active forms and racemates thereof, furthermore the corresponding N-oxides and the pharmaceutically acceptable acid addition salts of the free bases are also embraced by the scope of the invention.

The term "lower alkyl" as used in connection with the new compounds according to the invention refers to straight-chained or branched alkyl group with 1 to 5 carbon atoms, whereas the term "halogen" embraces bromine, chlorine and fluorine atoms.

In the compounds of the general formula (I) $R^1$ and $R^2$ each may represent e.g. methyl, ethyl, n-propyl, isopropyl, butyl or amyl group, furthermore fluorine, chlorine or bromine atom. Thus the substituted phenyl group appearing in these compounds may be e.g. a 2,6-dimethylphenyl, 2,6-diethylphenyl, 2-ethyl-6-methyl-phenyl, 2-chloro-6-methyl-phenyl or 2,6-dichlorophenyl group. $R^3$ may represent e.g. hydrogen atom or a methyl, ethyl, n-propyl, isopropyl, butyl, amyl, methanesulfonyl, ethanesulfonyl, benzenesulfonyl, p-toluenesulfonyl, formyl, acetyl, trichloroacetyl, trifluoroacetyl, propionyl, benzoyl, methoxycarbonyl or ethoxycarbonyl group. $R^4$ and $R^5$ each may represent e.g. hydrogen atom or a methyl, n-propyl, isopropyl, butyl or amyl group. $R^6$ and $R^7$ each may stand e.g. for hydrogen atom, a methyl, ethyl, n-propyl, isopropyl, butyl, amyl, 2-hydroxyethyl, 3-hydroxy-n-propyl, hydroxyisopropyl, 2-chloroethyl, 3-chloro-n-propyl, chloroisopropyl, methanesulfonyl, ethanesulfonyl, benzenesulfonyl, p-toluenesulfonyl, formyl, acetyl, glycyl, N,N-dimethylglycyl, N,N-diethylglycyl, propionyl, methoxycarbonyl or ethoxycarbonyl group, or they may form, together with the adjacent nitrogen atom, e.g. an aziridin-1-yl, azetidin-1-yl, piperidin-1-yl, piperazin-1-yl, 4-methyl-piperazin-1-yl, 1,4-oxazin-4-yl, 1,4-thiazin-4-yl or a phthalimido group.

Some of the compounds having the general formula (I) have already been reported in the literature. Thus D. I. Barron et al. [J. Med. Chem. 6, 705 (1963)] described the following compounds as substances with hypotensive effects: N-(2,6-dimethylphenyl)-ethylenediamine, a substance prepared by the hydrazinolysis of the respective phthalimido compound, furthermore N-methyl-N-(2,6-dimethylphenyl)-ethylenediamine and N-ethyl-N-(2,6-dimethylphenyl)-ethylenediamine, prepared by the reduction of the respective N-formyl or N-acetyl compound with lithium aluminium hydride.

P. P. Koelzer and K. H. Wehr [Arzneimittelforschung 8, 708 (1958)] mention 1-(2,6-dimethylphenyl-amino)-2-diethylamino-ethane and 1-[N-(2,6-dimethylphenyl)-acetamido]-2-diethylamino-ethane as compounds with local anaesthetic effects.

The Swedish patent specification No. 130, 104 [Chem. Abstr. 45, 5183i (1951)] reports on compounds with local anaesthetic effects. These compounds correspond to the general formula Ar—N($R^1$)—$R^2$—$NR^3R^4$, wherein Ar is a phenyl group having two or three lower alkyl substituents in various positions (among others, in positions 2 and 6 as well), $R^1$ is hydrogen or a lower alkyl group, $R^2$ is an alkylene group and $R^3$ and $R^4$ each stand for hydrogen or a lower alkyl group or they form, together with the adjacent nitrogen atom, a heterocyclic group. This reference describes the preparation of 1-(2,6-dimethylphenyl-amino)-2-dimethylamino-ethane and 1-(2,6-dimethylphenyl-amino)-2-diethylamino-ethane: these compounds are prepared by alkylating 2,6-dimethyl-formanilide with β-diethylamino-ethyl chloride or β-dimethylamino-ethyl chloride, and removing the formyl group of the resulting substance by acidic hydrolysis.

The compounds described in the above Swedish patent specification are different in structure from the new compounds having the general formula (I), since the $R^2$ alkylene chain which links the two nitrogen atoms in the known compounds is 1,2-ethylene or 1,1-propylene group, whereas the —CH($R^4$)—(CH$_2$)$_n$—CH($R^5$)-/alkylene chain of the new compounds cannot be 1,2-ethylene or 1,1-propylene.

A. Larizza and A. Pellegrino [Gazz. Chim. Ital. 89, 2018 (1959)] described compounds of the general formula (I), wherein $R^4$ and $R^5$ stand for hydrogen and n represents zero. These compounds possess local anaesthetic effects. 1-Diethylamino-2-(2,6-dimethylphenylamino)-propane and 1-diethylamino-2-(2,6-dimethylphenyl-amino)-butane were also mentioned in this reference. All of these compounds were prepared from 2,6-dimethylaniline and the respective haloalkylamines.

It should be noted that the compounds of the general formula (I) mentioned in the above references are outside the scope of the present invention.

Apart from those mentioned above, numerous N-arylalkylenediamine derivatives have been described in the literature in which the aromatic ring is unsubstituted, monosubstituted, or disubstituted in positions other than those indicated in the general formula (I). Of these known compounds e.g. 1-amino-2-phenylamino-propane, a substance acting on the sympathic nervous system (J. P. Fourneau: Bull. Soc. Chim. France 1940, 603), and 1-(3-chlorophenyl-amino)-2-diethylamino-ethane, a substance which stimulates the respiratory centre (J. P. Fourneau and Y. Lestrange: Bull. Soc. Chim. France 1947, 827), are to be mentioned. Several other structurally related compounds have also been described in the literature, wherein the positions of the substituents attached to the aromatic ring differ from those indicated for the new compounds, without attributing any biological effect to them [see e.g. T. Ueda and K. Ishizaki: Chem. Pharm. Bull. 15, 228 (1967); W. B. Wright et al.: J. Org. Chem. 26, 476, 485, 4051, 4057 (1966); published German patent application No. 2,205,745].

No anti-arrhythmic effect was mentioned in the literature in connection with any of the above compounds.

Now it has been found, unexpectedly, that the new compounds of the general formula (I) possess valuable biological effects, more particularly, they eliminate the disorders of cardiac rhythm, i.e. they are of anit-arrhythmic activity.

The new compounds of the general formula (I) are prepared according to the invention by the following methods:

(a) a compound of the general formula (II),

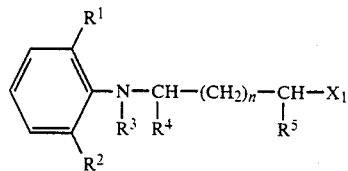
(II)

wherein $R^1$, $R^2$, $R^3$, $R^4$, $R^5$ and n are as defined above and $X_1$ stands for halogen, a lower aliphatic sulfonyloxy group or an aromatic sulfonyloxy group, is reacted with a compound of the general formula (III),

NMR$^6$R$^7$ (III)

wherein $R^6$ and $R^7$ are as defined above and M stands for hydrogen or an alkali metal atom; or (b) a compound of the general formula (IV),

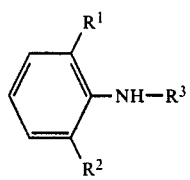
(IV)

wherein $R^1$, $R^2$ and $R^3$ are as defined above, is reacted with a compound of the general formula (V),

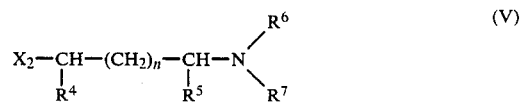
(V)

wherein $R^4$, $R^5$, $R^6$, $R^7$ and n are as defined above and $X_2$ stands for halogen, a lower aliphatic sulfonyloxy group or an aromatic sulfonyloxy group; pr (c) a compound of the general formula (VI),

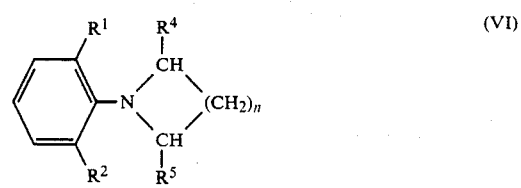
(VI)

wherein $R^1$, $R^2$, $R^3$, $R^4$, $R^5$ and n are as defined above, is reacted with a compound of the general formula (III), wherein $R^6$, $R^7$ and M are as defined above; or (d) the carbonyl group of a compound of the general formula (VII),

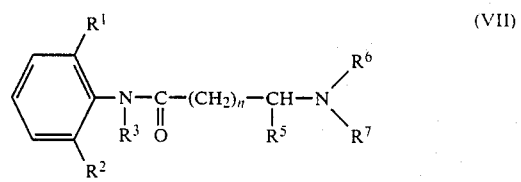
(VII)

wherein $R^1$, $R^2$, $R^3$, $R^5$, $R^6$, $R^7$ and n are as defined above, is reduced;

and, if desired, the acyl and/or sulfonyl group(s) of a resulting compound of the general formula (I), wherein $R^3$ and/or $R^6$ and/or $R^7$ represent an acyl or sulfonyl group, is(are) split off, the acyl group of a resulting compound of the general formula (I), wherein $R^3$ and/or $R^6$ and/or $R^7$ represent an acyl group, is reduced, a resulting compound of the general formula (I) is converted into its N-oxide, a resulting compound of the general formula (I), wherein at least one of $R^3$, $R^6$ and $R^7$ represents hydrogen, is acylated or alkylated, a compound of the general formula (I), obtained as a mixture of structural and/or optical isomers, is treated to separate the individual isomers from each other, a free base of the general formula (I) is converted into its acid addition salt, and/or a free base of the general formula (I) is liberated from its salt.

Method (a) is performed preferably so that a compound of the general formula (II) is reacted at 50° to 180° C. with a compound of the general formula (III). The reaction can be conducted either in the absence or in the presence of an appropriate solvent medium, such as acetone, methyl-ethylketone, dimethyl formamide, benzene or a homologue thereof, optionally in the present of a catalytic amount of an alkali metal iodide, such as potassium iodide.

If a compound of the general formula (II), wherein $R^3$ is hydrogen or a lower alkyl group, one of $R^4$ and $R^5$ stands for hydrogen and the other represents a lower alkyl group, and n is zero, is applied as starting substance, this compound converts temporarily into the respective aziridinium ion under the conditions of the reaction. Since the aziridine ring can open in two ways, a mixture of two compounds having the general formula (I) is obtained as end-product. These compounds are structural isomers, where $R^4$ is hydrogen and $R^5$ is a lower alkyl group in one of the isomers, and $R^4$ is a lower alkyl group and $R^5$ is hydrogen in the other.

The compounds of the general formula (II), applied as starting substances in the above process, can be prepared as follows:

A compound of the general formula (IV), wherein $R^1$, $R^2$ and $R^3$ are as defined above, is reacted with a cyclic ether of the general formula (VIII),

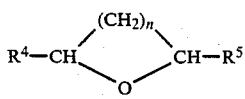  (VIII)

wherein $R^4$, $R^5$ and n are as defined above, or with a halohydrine obtained by splitting the above cyclic ether with a hydrogen halide, and the hydroxy group of the resulting compound of the general formula (IX),

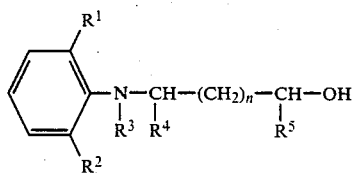  (IX)

wherein $R^1$, $R^2$, $R^3$, $R^4$, $R^5$ and n are as defined above, is halogenated or sulfonylated in a manner known per se to obtain the required compound of the general formula (II).

The compounds of the general formula (II) can also be prepared from the compounds of the general formula (IV) in a single step, by reacting them with a compound of the general formula (X),

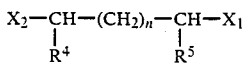  (X)

wherein $R^4$, $R^5$, n, $X_1$ and $X_2$ are as defined above.

The compounds of the general formula (III) are commercially available substances. The starting substances of the general formula (IV) are also commercially available, or can be prepared by methods well known in the art [see e.g. M. A. Bambenek: Rec. Trav. Chim. 82, 97 (1963)].

The compounds of the general formula (VIII) are commercially available substances or can be prepared by methods known in the art [see e.g. S. Searles et. al.: J. Am. Chem. Soc. 79, 948 (1957), L. F. Schmoyer and L. C. Case: Nature 187, 592 (1960)].

the compounds of the general formula (X) are commercially available substances or can be prepared according to known methods [see e.g. M. Sletzinger et al.: J. Am. Chem. Soc. 74, 5619 (1952)].

According to a preferred variant of Method (b) a compound of the general formula (IV), wherein $R^3$ is hydrogen or lower alkyl, and the other substituents are as defined above, is reacted with a compound of the general formula (V) under the conditions mentioned in connection with Method (a).

The compounds of the general formula (IV) in which $R^3$ is an acyl or sulfonyl group as defined above can be reacted with compounds of the general formula (V) preferably in an appropriate solvent medium, such as acetone, dimethyl formamide, benzene or a homologue thereof, at 50° to 150° C., in the presence of one equivalent of a methal hydride, such as sodium hydride, calculated for the amount of the starting substance of the general formula (IV).

If a compound of the general formula (V), wherein one of $R^4$ and $R^5$ is hydrogen and the other stands for a lower alkyl group, n is equal to zero, and $R^6$ and $R^7$ are other than an acyl or a sulfonyl group, or the $—NR^6R^7$ group is other than phthalimido, is applied as starting substance, this compound converts temporarily into the respective aziridinium ion under the conditions of the reaction. Since the aziridine ring can open in two ways, a mixture of two compounds having the general formula (I) is obtained as end-porduct. These compounds are structural isomers, where $R^4$ is hydrogen and $R^5$ is a lower alkyl group in one of the isomers, and $R^4$ is a lower alkyl group and $R^5$ is hydrogen in the other.

The starting substances of the general formula (V) are known compounds or can be prepared by methods known in the art [see e.g. M. Sletzinger et al.: J. Am. Chem. Soc. 74, 5619 (1952)].

Method (c) of the invention is performed preferably so that a compound of the general formula (VI) is reacted with 2 to 10 equivalents of a compound of the general formula (III) at 100° to 200° C., either in an appropriate solvent medium, such as dimethyl formamide, dimethyl acetamide or dimethyl sulfoxide, or in the absence of a solvent.

If a compound of the general formula (VI), in which one of $R^4$ and $R^5$ is hydrogen and the other is a lower alkyl group and n is zero, is applied as starting substance, this cyclic imine can be opened in two ways, and a mixture of two compounds of the general formula (I) is obtained as end-product. These compounds are structural isomers, where $R^4$ is hydrogen and $R^5$ is a lower alkyl group in one of the isomers, and $R^4$ is a lower alkyl group and $R^5$ is hydrogen in the other.

The starting substances of the general formula (VI) are known compounds or can be prepared by methods known in the art [see e.g. H. W. Heine et al.: J. Am. Chem. Soc. 76, 1173, 2503 (1954)].

According to a preferred variant of Method (d) a compound of the general formula (VII) is reduced with a metal hydride, particularly with a complex metal hydride, such as lithium aluminium hydride, in an etheral solvent, such as diethyl ether, tetrahydrofuran or dioxane, at a temperature of 0° to 100° C.

The starting substance of the general formula (VII) are known compounds or can be prepared by methods known in the art [see e.g. E. W. Byrnes et al.: J. Med. Chem. 22, 1171 (1979)].

A compound of the general formula (I) in which $R^3$ and/or $R^6$ or $R^7$ is a sulfonyl group as defined above can be desulfonylated preferably so that the sulfonyl compound is treated with hydrogen formed in situ from an aliphatic alchohol (such as n-butanol, n-amylalcohol or isoamylalcohol) and an alkali metal (such as potassium or sodium) at a temperature of 100° to 150° C.

A compound of the general formula (I) in which $R^3$ and/or $R^6$ or $R^7$ is an acyl group as defined above can be deacylated preferably so that the acyl derivative is contacted with a strong mineral acid, such as hydrochloric acid or sulfuric acid, at a temperature of 80° to 150° C. The reaction can be performed in a solvent medium, such as a lower alkanol (e.g. ethanol, propanol or butanol) or acetic acid, or the excess of the strong acid can be applied as reaction medium.

A compound of the general formula (I) in which group $-NR^6R^7$ stands for a residue derived from the imide of a dicarboxylic acid, such as phthalimido group (i.e. $R^6$ and $R^7$ form together a phthaloyl group), can be converted into the respective deprotected derivative so that the protected compound is treated with 2 to 5 equivalents of hydrazine in a lower alkanol, such as methanol, ethanol or propanol, at a temperature of 50° to 100° C. This method is particularly preferred for the removal of the phthaloyl group.

When $R^3$ and $R^6$ or $R^7$ stand for groups of the same character (e.g. acyl groups), these protecting groups are split off preferably in a single step, under the same reaction conditions. If, however, $R^3$ and $R^6$ and/or $R^7$ are protecting group different in character, e.g. $R^3$ is a sulfonyl group and $R^6$ and $R^7$ form together a phthaloyl group, it is preferred to split off the phthaloyl group first as described above, and then to remove the sulfonyl group in a separate step.

The acyl group of a compound of the general formula (I) in which $R^3$ and/or $R^6$ or $R^7$ represent an acyl group as defined above can be reduced into the respective hydrocarbon group preferably under the conditions described in connection with Method (d).

The processes according to the invention yield the compounds of the general formula (I) generally as free bases. These free bases can be converted into their acid addition salts preferably by dissolving the base in an appropriate solvent, such as methanol, isopropanol, diethyl ether or a mixture thereof, and admixing this solution with a solution of the selected acid. The salts can be separated either directly by filtration or by the partial or total removal of the solvent.

The free bases of the general formula (I) can be liberated from their salts preferably so that the salt is dissolved in an appropriate solvent, such as water, methanol, ethanol or a mixture thereof, the solution is rendered alkaline e.g. with an aqueous sodium hydroxide or ammonium hydroxide solution, and the liberated base is extracted from the reaction mixture with chloroform or benzene.

If the compounds of the general formula (I) are obtained as mixtures of isomers, the individual isomers can by separated from their mixtures by conventional methods. Thus e.g. the salts of the isomers can be subjected to fractional crystallization, or the isomers can be separated by column chromatography. When $R^6$ and $R^7$ stand for hydrogen in each of the isomers, the isomers can be separated from one another via their derivatives, so that the isomeric mixture is acylated first with an appropriate acyl chloride, such as p-toluenesulfonyl chloride, or converted into a Schiff-base with an appropriate carbonyl compound, such as benzaldehyde or o-chloro-benzaldehyde. The isomeric mixture of the acyl derivatives or Schiff-bases is subjected then to a conventional separation method, such as crystallization, layer chromatography or column chromatography, and the resulting pure isomers are reconverted into the starting free amines. In this step the sulfonylated derivatives can be desulfonylated as described above, by treating them with metallic sodium or potassium in a lower alkanol, whereas the Schiff-bases can be converted into the free amines by treating them with an aqueous mineral acid, such as hydrochloric acid or sulfuric acid, in a lower alkanol at room temperature.

The compounds of the general formula (I) in which $R^4$ or $R^5$ is other than hydrogen contain an asymmetric carbon atom, thus they may exist in the form of optically active isomers and racemates. The pure optically active isomers of these compounds can be separated from the respective isomeric mixtures preferably as follows. The mixture of isomers (e.g. the racemate) is treated with 0.5 to 1.0 molar equivalents of a conventional optically active acid, such as D-tartaric acid, O,O-dibenzoyl-D-tartaric acid, O,O-dibenzoyl-D-tartaric acid semi-dimethylamide or thiazolidine-4-carboxylic acid, the salt of one of the optically active isomers is separated, and the mother liquors are processed to obtain the other isomer either as a free base or as its salt, depending on the amount of the acid utilized. The salt of the optically active isomer separated in the first step can be recrystallized in one or more steps to obtain an optically pure substance; however, depending on the amount of the acid applied, an optically pure substance can also be obtained directly. Any of the salts can be converted into the respective free, optically pure base as described above, whereafter, if deisred, the base can be converted into its pharmaceutically acceptable acid addition salt.

As mentioned above, the compounds of the general formula (I) possess valuable anti-arrhythmic effects.

The anti-arrhythmic effects of the compounds according to the invention were examined by the following methods:

1. Aconitin-Induced Arrhythmia In Mice

Arrhythmia was induced in male mice, weighing 20-25 g, by treating them continuously, at a rate of 0.2 ml/min, with an infusion containing 5 /ug/kg of aconitin. The test compound was administered to the animals either intraperitoneally 15 minutes before the start of the infusion, or orally 60 minutes before the start of the infusion. The time of the appearance of arrhythmia was recorded, and the percentage delay was calculated in relation to the data obtained in the controls, pre-treated with 0.9% sodium chloride solution only [B. Vargaftig and J. L. Coignet: European J. of Pharmacol. 6, 49-55 (1969); N. K. Dadkar and B. K. Bhattachariya: Arch. Int. Pharmacodyn. 212, 297-301 (1974); D. U. Nwagwu, T. L. Molcslaw and S. J. Stohs: Arch. Int. Pharmacodyn. 229, 219-226 (1977)].

The results are listed in Tables 1 and 2.

1-(2,6-Dimethylphenoxy)-2-aminopropane hydrochloride and N-(diethylamino-acetyl)-2,6-dimethylaniline hydrochloride were applied as reference substances. The $ED_{50}$ values represent the doses which provoke 50% delay in the appearance time of arrhythmia. The $ED_{50}$ and $LD_{50}$ values were calculated according to the method of Litchfield and Wilcoxon [J. Pharmacol. Exp. Ther. 96, 99-113 (1949)].

TABLE 1

Examination of the anti-arrhythmic effect in anaesthetized mice treated with aconitin, with intraperitoneal administration of the test compounds

| Compound | Dose mg/kg i.p. | Delay in the appearance time of arrhythmia, % | Number of animals | $LD_{50}$ mg/kg i.p. | $\dfrac{LD_{50}}{ED_{50}}$ |
|---|---|---|---|---|---|
| 1-(2,6-Dimethylphenoxy)-2-amino-propane hydrochloride (reference substance) | 5<br>10<br>25<br>50<br>75 | +3.5<br>+7.7<br>+33.3<br>+83.1<br>+162.4 | 20<br>20<br>20<br>20 | 114 | 3.68 |
| N-Diethylamino-acetyl)-2,6-dimethyl-aniline hydrochloride (reference substance) | 5<br>10<br>25<br>40 | +1<br>+16.2<br>+33.7<br>+70.1 | 20 | 132 | 4.13 |
| An about 2:5 mixture of 1-(2,6-dimethylphenyl-amino)-2-aminopropane dihydrochloride and 1-amino-2-(2,6-dimethylphenyl-amino)-propane dihydrochloride | 25<br>50<br>100 | +30.2<br>+72.2<br>+147.4 | 16<br>17<br>16 | 156 | 4.22 |
| 1-(2,6-Dimethylphenyl-amino)-2-amino-propane dihydrochloride | 25<br>50<br>100 | +17.0<br>+87.3<br>+124.2 | 15<br>18<br>15 | 135 | |
| 1-Amino-2-(2,6-dimethylphenyl-amino)-propane dihydrochloride | 25<br>50<br>100 | +16.6<br>+60.0<br>+126.7 | 15<br>17<br>15 | 155 | |
| An about 1:1 mixture of 1-(2-chloro-6-methyl-phenyl-amino)-2-amino-propane hydrochloride and 1-amino-2-(2-chloro-6-methyl-phenyl-amino)-propane hydrochloride | 10<br>25<br>50<br>75 | +26.8<br>+42.8<br>+126.5<br>+164.7 | 18<br>18<br>15<br>15 | 119 | |
| 1-(2,6-Dimethylphenyl-amino)-2-dimethyl-amino-propane dihydrochloride | 10<br>25<br>50<br>75 | +17.2<br>+72.7<br>+138.3<br>+211.9 | 15<br>15<br>17<br>15 | 114 | 5.7 |
| 1-(2,6-Dimethylphenyl-amino)-2-amino-butane dihydrochloride | 10<br>25<br>50<br>75 | +3.0<br>+40.8<br>+104.0<br>+149.0 | 13<br>17<br>17<br>15 | | |
| 1-(2,6-Dimethylphenyl-amino)-3-amino-butane dihydrochloride | 10<br>25<br>50<br>75 | 0<br>+48.0<br>+87.0<br>+135.0 | 13<br>12<br>14<br>5 | | |
| 1-[N-Methyl-N-(2,6-dimethylphenyl)-amino]-2-dimethylamino-propane hydrochloride | 50 | +78.0 | 5 | | |

TABLE 2

Examination of the anti-arrhythmic effect in anaesthetized mice treated with aconitin, with oral administration of the test compounds

| Compound | Dose mg/kg p.o. | Delay in the appearance time of arrhythmia, % | Number of animals |
|---|---|---|---|
| An about 2:5 mixture of 1-(2,6-dimethylphenyl-amino)-2-aminopropane dihydrochloride and 1-amino-2-(2,6-dimethylphenyl-amino)-propane dihydrochloride | 100 | +42.0 | 37 |
| 1-(2,6-Dimethylphenyl-amino)-2-amino-propane dihydrochloride | 100 | +27.0 | 18 |
| 1-Amino-2-(2,6-dimethylphenyl-amino)-propane dihydrochloride | 100 | +41.0 | 18 |
| 1-(2,6-Dimethylphenyl-amino)-3-amino-butane dihydrochloride | 100 | +84.0 | 19 |
| An about 1:1 mixture of 1-(2-chloro-6-methyl-phenyl-amino)-2-amino-propane hydrochloride and 1-amino-2-(2-chloro-6-methyl-phenyl-amino)-propane hydrochloride | 100 | +26.0 | 22 |
| 1-(2,6-Dimethylphenyl-amino)-2-dimethylamino-propane dihydrochloride | 100 | +74.0 | 20 |
| 1-(2,6-Dimethylphenyl-amino)-2-amino-butane dihydrochloride | 100 | +33.0 | 17 |
| N-(Diethylamino-acetyl)-2,6-dimethyl-aniline hydrochloride (reference substance) | 100 | +38.0 | 22 |
| 1-(2,6-Dimethylphenoxy)-2-amino-propane hydrochloride (reference substance) | 100 | +82.0 | 20 |

2. Ouabain-Induced Arrhythmia In Dogs

Anaesthetized dogs of both sexes were treated intravenously with an infusion of 60 /ug/kg of ouabain to provoke arrhythmia, and the arrhythmic state was maintained with an ouabain dose 60 times less than the initial. In this way a ventricular tachycardia or tachyarrhythmia lasting for more than 180 minutes was provoked. The compounds were tested during this period. The period of recovered normal sinus rhythm was recorded, and when a compound exerted protective effect for more than 30 minutes, this fact was regarded as complete protection. The tests were performed essentially according to the method of Piascik et al. [Can. J. of Physiol. and Pharmacol. 57, 1350–1358 (1979)].

The results are listed in Table 3.

TABLE 3

Examination of the anti-arrhythmic effect in dogs anaesthetized with a 30 mg/kg i.v. dose of pentobarbital sodium and treated with ouabain

| Compound | Dose mg/kg i.v. | Complete suspension Number of cases | Average time of partial suspension, min. | Number of animals |
|---|---|---|---|---|
| 1-(2,6-Dimethylphenoxy)-2-amino-propane hydrochloride (reference substance) | 0.5 | 1/15 | 0.5 | 14 |
|  | 1.0 | 1/15 | 2.6 | 14 |
|  | 2.0 | 3/14 | 2.9 | 11 |
|  | 4.0 | 4/9 | 1.4 | 5 |
|  | 8.0 | 2/5 | 10.3 | 3 |
| N-(Diethylamino-acetyl)-2,6-dimethyl-aniline hydrochloride (reference substance) | 0.5 | 0/15 | 0.5 | 15 |
|  | 1.0 | 0/15 | 1.6 | 16 |
|  | 2.0 | 1/15 | 2.5 | 14 |
|  | 4.0 | 3/14 | 2.5 | 11 |
|  | 8.0 | 2/11 | 7.5 | 9 |
| 1-(2,6-Dimethylphenyl-amino)-2-dimethylamino-propane dihydrochloride | 0.5 | 0/15 | 0.4 | 15 |
|  | 1.0 | 0/15 | 1.5 | 15 |
|  | 2.0 | 4/15 | 5.7 | 11 |
|  | 4.0 | 3/12 | 6.4 | 9 |
|  | 8.0 | 5/9 | 10.0 | 4 |
| 1-(2,6-Dimethylphenyl-amino)-3-amino-butane dihydrochloride | 0.5 | 1/16 | 0.3 | 15 |
|  | 1.0 | 1/15 | 0.8 | 14 |
|  | 2.0 | 2/15 | 3.7 | 13 |
|  | 4.0 | 7/14 | 5.4 | 7 |
|  | 8.0 | 3/5 | 6.5 | 2 |

3. Barium Chloride-Induced Arrhythmia In Awake Rabbits 6 mg/kg of barium chloride were injected into the ear vein of awake rabbits, which provoked an arrhythmia lasting for 20 minutes on the average. The compounds to be tested were administered intravenously to the animals 3 minutes after treating them with barium chloride, and the effect was recorded. It was regarded as a positive protecting effect when the compound suspended the arrhythmic condition for at least 3 minutes. The tests were performed essentially according to the method of Papp and Szekeres [Acta Physiologica Academiae Scientiarum Humg., Tomus 32(4), 365–375 (1967)].

The results are listed in Table 4.

TABLE 4

Effects on barium chloride induced arrhythmia in awake rabbits, upon administering the compounds in an i.v. dose of 2 mg/kg

| Compound | Protecting effect Number of animals |
|---|---|
| 1-(2,6-Dimethylphenoxy)-2-amino-propane hydrochloride (reference substance) | 4/10 |
| N-(Diethylamino-acetyl)-2,6-dimethyl-aniline hydrochloride (reference substance) | 2/10 |
| 1-(2,6-Dimethylphenyl-amino)-2-dimethylamino-propane dihydrochloride | 5/10 |
| 1-(2,6-Dimethylphenyl-amino)-3-amino-butane dihydrochloride | 5/10 |

4. Determination of the Fibrillation Threshold In Anaesthetized Cats

The chests of the cats were opened under chloralose-urethane anaesthesia a bipolar stimulating electrode was fixed onto the heart, and the heart was stimulated electrically with a frequency of 20 Hz, under continuously increasing current strength, until a fibrillo-flattern could be observed. This current strength was regarded as the fibrillation threshold of the animal. Thereafter the test compounds were administered, and the increases in the fibrillation threshold value was recorded [see Szekeres and Papp: Experimental Cardiac Arrhythmias and Antiarrhythmic Drugs; Academic Press, Budapest, 1971].

The results are listed in Table 5.

TABLE 5

Effects on the fibrillation threshold measured in anaesthetized cats

| Compound | Number of animals | Dosis mg/kg i.v. | Effect % |
|---|---|---|---|
| 1-(2,6-Dimethylphenoxy)-2-amino-propane hydrochloride (reference substance) | 6 | 0.5 | +9.4 |
|  |  | 1.0 | +12.9 |
|  |  | 2.0 | +24.8 |
|  |  | 4.0 | +34.0 |
| N-(Diethylamino-acetyl)-2,6-dimethyl-aniline hydrochloride (reference substance) | 6 | 0.5 | 0 |
|  |  | 1.0 | +2.0 |
|  |  | 2.0 | +17.7 |
|  |  | 4.0 | +39.1 |
| 1-(2,6-Dimethylphenyl-amino)-2-dimethylamino-propane dihydrochloride | 7 | 0.5 | +8.6 |
|  |  | 1.0 | +12.2 |
|  |  | 2.0 | +27.0 |

TABLE 5-continued

| Effects on the fibrillation threshold measured in anaesthetized cats | | | |
|---|---|---|---|
| Compound | Number of animals | Dosis mg/kg i.v. | Effect % |
| 1-(2,6-Dimethylphenyl-amino)-3-amino-butane dihydrochloride | 5 | 4.0 | +53.9 |
| | | 0.5 | +2.3 |
| | | 1.0 | +3.0 |
| | | 2.0 | +16.5 |
| | | 4.0 | +52.9 |

5. Electrophysiological Tests Performed On Isolated Heart

Heart of rabbits of both sexes, weighing 1–2 kg, were removed, the right and left auricles and a segment of the right ventricle were prepared and placed into a vessel filled with nutrient solution. Bipolar platinum electrodes (a stimulating electrode and a lead electrode) were placed onto the organ strips, and the electric stimulus threshold and the speed of impulse condution were measured. The effective refractory period determined on the basis of the maximum driving frequency. The results were read from the screen of an oscilloscope (see Szekeres and Papp: Experimental Cardiac Arrhythmias; Academic Press, Budapest, 1971).

The results are listed in Table 6.

animals were respirated artifically, their chests were opened, and a strain gage was sutured on the left heart. The strain gage was connected to the Hellige recorder, and the variations in cardiac contractile force were recorded. The test compounds were administered to the animals intravenously through a cannula.

The results are listed in Table 7.

b. Examination of the Effects Exerted on the Systemic and Pulmonary Circulation of Awake Cats Cats were anaesthetized with pentobarbital, and cannulas were placed into the carotis artery and, through the jugular vein, into the pulmonary artery. An additional cannula was placed into the jugular vein for the administration of the test compound. The cannulas were filled up with heparin in order to avoid blood clotting.

TABLE 6

| Electrophysiological effects on isolated rabbit heart | | | | | | |
|---|---|---|---|---|---|---|
| | Left auricle Change of the | | | Right ventricle Change of the | | |
| Compound | electric stimulus threshold | effective refractory period | conduction time | electric stimulus threshold | effective refractory period | conduction time |
| 1-(2,6-Dimethylphenoxy)-2-amino-propane hydrochloride (reference substance) 2 mg/l | +36% n = 7 | +32% n = 5 | +24% n = 6 | +14% n = 10 | +28% n = 5 | +11% n = 6 |
| 1-(2,6-Dimethylphenyl-amino)-2-dimethylamino-propane dihydrochloride 2 mg/l | +32% n = 6 | +20% n = 6 | +12% n = 6 | +6% n = 7 | +18% n = 5 | +12% n = 4 |

Remarks:
The data listed in Table 6 are average values.
n = number of tests.

6. Examination of the Cardiovascular Effects a. Examination of Inotropic Effects in Anaesthetized Cats Cats were anaesthetized with chloralose-urethane, a cannula was lead into the femoral artery, and the cannula was connected, through a Statham P 23 Db pressure sensor, to a Hellige recorder, where the arterial blood pressure and the pulse rate were recorded. The Thereafter the wounds were sutured, and the cannulas were led below a bandage placed around the neck of the animal. 3 days after this operation the systemic arterial blood pressure, the pulmonary arterial pressure and the pulse rate of the awake animals were measured with a Hellige recorder, connected to the cannulas through a Statham P 23 Db type pressure transducer.

The results are listed in Table 8.

TABLE 7

| Effects exerted on the myocardial contractile force of anaesthetized cats | | | | | | | |
|---|---|---|---|---|---|---|---|
| Compound | Dose mg/kg i.v. | Arterial blood pressure mmHg | | Pulse/minute | | Contractility % | |
| | | Basal | Change | Basal | Change | Basal | Change |
| 1-(2,6-Dimethylphenoxy)-2-amino-propane hydrochloride (reference substance) | 0.5 | 115 | −45 | 170 | −40 | 100 | −29 |
| | 1.0 | 125 | −40 | 200 | −50 | 100 | −32 |
| | 2.0 | 110 | −60 | 140 | −50 | 100 | −38 |
| | 5.0 | 110 | −65 | 150 | −50 | 100 | −57 |
| 1-(2,6-Dimethylphenyl-amino)-2-dimethylamino-propane dihydrochloride | 0.5 | 110 | −7 | 140 | +10 | 100 | −5 |
| | 1.0 | 95 | −10 | 140 | +15 | 100 | +4/−6 |
| | 2.0 | 110 | −30 | 175 | −10 | 100 | +10/−5 |
| | 5.0 | 106 | −40 | 140 | −25 | 100 | −33 |

TABLE 8

| | Pulmonary and systemic arterial effects in awake cats | | | | | | |
|---|---|---|---|---|---|---|---|
| | Dose mg/kg | Arterial blood pressure mmHg | | Pulmonary arterial mean pressure* | | Pulse/minute | |
| Compound | i.v. | Basal | Change | Basal | Change | Basal | Change |
| 1-(2,6-Dimethylphenoxy)-2-amino-propane hydrochloride (reference substance) | 1.0 | 102 | −39 | 13 | +6 | 190–200 | −66 |
| 1-(2,6-Dimethylphenyl-amino)-2-dimethylamino-propane dihydrochloride | 1.0 | 102 | +2 | 13 | +2.8 | 190–200 | −9 |

*mmHg

It appears from the above tables that some of the compounds according to the invention are superior in anti-arrhythmic activity to the presently applied anti-arrhythmic drugs. As an additional advantage, the new compounds are devoid of the undesired circulatory side effects generally appearing upon the administration of/the known anti-arrhythmic agents; thus they do not provoke a pressure drop in the systemic circulation, a pressure increase in the pulmonary circulation and have no bradycardial side-effects.

The new compounds according to the invention can be applied as substances for eliminating the arrhythmic states of mammals, including humans. For this purpose the compounds can be administered either enterally or parenterally in the form of appropriate pharmaceutical compositions, preferably tablets, capsules, coated tablets or injections.

The invention also relates to pharmaceutical compositions containing as active ingredient at least one compound of the general formula (I) or an N-oxide or pharmaceutically acceptable acid addition salt thereof, together with one or more conventional pharmaceutical carrier, diluent and/or additive. If desired, the pharmaceutical compositions may also contain other biologically active substances, particularly other anti-arrhythmic agents.

The pharmaceutical compositions can be prepared by methods well known in the art.

The new compounds according to the invention can be administered generally in daily doses of about 1 to 10 mg/kg, the accurate dose being dependent on the body weight, age and general health condition of the patient.

The invention is elucidated in detail by the aid of the following non-limiting Examples.

EXAMPLE 1

Preparation of
1-(2,6-dimethylphenyl-amino)-2-amino-propane 6.1 g (0.27 g-atom) of metallic sodium are added in small portions, within about 2 hours, to a stirred solution of 10.25 g (40 mmoles) of 1-[N-(2,6-dimethylphenyl)-methanesulfonamido]-2-amino-propane in 200 ml of primary n-amyl-alcohol at 130°–135° C., and then the mixture is stirred at the same temperature for 15 minutes. The mixture is cooled, 10 ml of methanol are added dropwise, thereafter it is washed eight times with 50 ml of water, each, dried over anhydrous magnesium sulfate, filtered, and the solvent is evaporated under reduced pressure. The oily residue, weighing 6.62 g (yield: 93%), is distilled under reduced pressure. 5.6 g of pure 1-(2,6-dimethylphenyl-amino)-2-amino-propane are obtained; b.p.: 105°–107° C/80 Pa. Yield: 78.5%.

The free base is converted into its hydrochloride as follows: 5.6 g of the free base, obtained as described above, are dissolved in 30 ml of dry diethyl ether, and a mixture of 12 ml of a 15 w/v % isopropanolic hydrochloric acid solution and 30 ml of dry diethyl ether is added. The precipitate is filtered off, washed with diethyl ether, dried, and recrystallized then from methanol. 5.9 g of the pure dihydrochloride are obtained; m.p.: 237°–238° C.

EXAMPLES 2 to 10

The compounds of the general formula (I), wherein $R^3$ is hydrogen, listed in Table 9 are prepared from the appropriate methanesulfonyl derivatives as described ove.

TABLE 9

| Example No. | $R^1$ | $R^2$ | $R^4$ | $R^5$ | $R^6$ | $R^7$ | n | Base b.p. °C./Pa | Hydrochloride m.p. °C. |
|---|---|---|---|---|---|---|---|---|---|
| 2 | CH₃ | CH₃ | CH₃ | H | H | H | 0 | 112–114/66.7 | 229–230* |
| 3 | CH₃ | CH₃ | H | CH₃ | CH₃ | H | 0 | 110/53.3 | 169–170* |
| 4 | CH₃ | CH₃ | H | CH₃ | C₂H₅ | C₂H₅ | 0 | 122–126/40 | 110–120* |
| 5 | CH₃ | CH₃ | H | CH₃ | NR⁶R⁷ = 1-piperazinyl | | 0 | 168–172/80 | 142–146** |
| 6 | C₂H₅ | C₂H₅ | H | CH₃ | H | H | 0 | 110–114/80 | 235–237* |
| 7 | 90% CH₃ 10% CH₃ | CH₃ CH₃ | H CH₃ | CH₃ H | H H | H H | 1 1 | 110–112/66.7 | 229–231* |
| 8 | CH₃ | CH₃ | H | CH₃ | CH₃ | CH₃ | 0 | 114–116/53.3 | 173–174* |
| 9 | CH₃ | CH₃ | H | CH₃ | CH(CH₃)₂ | H | 0 | 116–117/80 | 172–174* |
| 10 | CH₃ | CH₃ | CH₃ | H | CH₃ | CH₃ | 0 | 130–132/93.3 | 185–188* |

*dihydrochloride
**trihydrochloride

EXAMPLE 11

Preparation of a mixture of
1-(2,6-dimethylphenyl-amino)-2-amino-propane and
1-amino-2-(2,6-dimethylphenyl-amino)-propane 72.5 g (0.237 moles) of an about 2:5 mixture of 1-(2,6-dimethylphenyl-amino)-2-phthalimido-propane and 1-phthalimido-2-(2,6-dimethylphenyl-amino)-propane are dissolved in 700 ml of ethanol at 60°–70° C., 70 ml of a 85% aqueous hydrazine hydrate solution are added to it, and the reaction mixture is boiled for one hour. Next day the separated phthalylhydrazide is filtered off, washed with ethanol, and the solvent is removed from the filtrate by evaporation under reduced pressure. The oily residue is distilled under reduced pressure. 29.85 g (71%) of an isomeric mixture, containing the title compounds in a ratio of about 2:5, are obtained; b.p.: 109°–112° C./66.7 Pa.

The resulting free base is converted into the dihydrochloride as described in Example 1. The salt melts at 213°–216° C.

The isomeric mixture of the starting phthalimido compounds is prepared as follows:

STEP A

Preparation of 1-(2,6-dimethylphenyl-amino)-2-chloropropane

A solution of 18.0 ml (29.7 g, 0.25 moles) of thionyl chloride in 50 ml of dry benzene is added dropwise, within 0.5 hours, to a suspension of 43.15 g (0.20 moles) of 1-(2,6-dimethylphenyl-amino)-2-propanol hydrochloride in 400 ml of dry benzene. The addition is performed at room temperature under nitrogen atmosphere. The reaction mixture is boiled for 3 hours, then the resulting solution is cooled to room temperature, and 50 ml of water are added dropwise to the mixture at a temperature not exceeding 20° C. Concentrated aqueous ammonia is added then dropwise to the mixture to adjust the pH of the aqueous phase to 9. The phases are separated from each other, and the aqueous phase is extracted twice with 100 ml of benzene, each. The benzene solutions are combined, washed thrice with 100 ml of water, each, dried over anhydrous magnesium sulfate, and the solvent is evaporated. The oily residue is distilled under reduced pressure. 27.6 g (70%) of 1-(2,6-dimethylphenyl)-amino-2-chloro-propane are obtained; b.p.: 99°–100° C./53.3 Pa.

STEP B

Preparation of a mixture of 1-(2,6-dimethylphenyl-amino)-2-phthalimido-propane and 1-phthalimido-2-(2,6-dimethylphenyl-amino)-propane A mixture of 70 g (0.35 moles) of 1-(2,6-dimethylphenyl-amino)-2-chloro-propane, prepared as described in Step (a) above, 700 ml of dimethyl formamide, 130 g (0.7 moles) of potassium phthalimide and 3.3 g (20 mmoles) of potassium iodide is stirred at 145°–150° C. for 4 hours, and then the mixture is cooled and poured onto 2 litres of ice water. The separated yellow, oily substance solidifies upon some hours of standing. The solid is filtered off, washed with water, dried and recrystallized from isopropanol. 72.9 g (67.6%) of the required isomeric mixture are obtained; m.p.: 90°–98° C.

EXAMPLES 12 AND 13

The compounds of the general formula (I), wherein $R^3$, $R^6$ and $R^7$ represent hydrogen and n is equal to zero, listed in Table 10 are prepared from the respective isomeric phthalimide compounds as described in Example 11. The end-products are obtained as mixtures of isomers.

TABLE 10

| Example No. | $R^1$ | $R^2$ | $R^4$ | $R^5$ | Percentage of the isomer | Base b.p. °C./Pa | Monohydrochloride m.p. °C. |
|---|---|---|---|---|---|---|---|
| 12 | CH₃ | C₂H₅ | H | CH₃ | 20 | 113–115/ 93.3 | 183–186 |
|  | CH₃ | C₂H₅ | CH₃ | H | 80 |  |  |
| 13 | CH₃ | Cl | H | CH₃ | 50 | 109–112/ | 178–182 |
|  | CH₃ | Cl | CH₃ | H | 50 | 53.3 |  |

The starting phthalimido compounds are prepared as described in Steps (a) and (b) of Example 11. The physical constants of the compounds are listed in Table 11.

TABLE 11

| Example No. | Isomeric mixture of the phthalimido compounds m.p. °C. (hydrochloride) | 1-Arylamino-2-chloro-propane b.p. °C./Pa |
|---|---|---|
| 12 | 165–168 | 108–112/93.3 |
| 13 | 127–129 | 108–110/40 |

EXAMPLE 14

Preparation of 1-(2,6-dimethylphenyl-amino)-2-diethylamino-propane and 1-diethylamino-2-(2,6-dimethylphenyl-amino)-propane

Method A

A mixture of 10.5 g (53 mmoles) of 1-(2,6-dimethylphenyl-amino)-2-chloro-propane, prepared as described in Step (a) of Example 11, 30 ml (21.3 g, 0.29 moles) of diethylamine and 0.5 g of potassium iodide is heated at 180° C. for 7 hours in a steel bomb. The mixture is allowed to cool, dissolved in 200 ml of a 1 n aqueous hydrochloric acid, and the solution is shaken thrice with 50 ml of ether, each. The aqueous-acidic phase is rendered alkaline with concentrated aqueous ammonia under ice cooling, and the alkaline solution is extracted thrice with 50 ml of chloroform, each. The chloroform solutions are combined, washed thrice with 50 ml of water, each, dried over anhydrous magnesium sulfate, and the solvent is evaporated under reduced pressure. 10.2 g (83.4%) of an isomeric mixture are obtained; the mixture contains the two title compounds in a ratio of about 1:3. B.p.: 105° C./26.6 Pa.

10.2 g of the above isomeric mixture are subjected to chromatography on a column filled with 600 g of silica gel; a 6:1 mixture of benzene and pyridine is applied as eluant. 0.9 g of pure 1-(2,6-dimethylphenyl-amino)-2-diethylamino-propane ($R_f$=0.7 when subjected to thin layer chromatography on silica gel in a 6:1 mixture of benzene and pyridine; the dihydrochloride of the compound, prepared as described in Example 1, melts at 112°–120° C.) and 2.7 g of pure 1-diethylamino-2-(2,6-dimethylphenyl-amino)-propane ($R_f$=0.6 when subjected to thin layer chromatography in the above system; the dihydrochloride of the compound, prepared as described in Example 1, melts at 150°–154° C.) are obtained.

Method B

A mixture of 3.25 g (20 mmoles) of 1-dimethylphenyl)-2-methyl-aziridine and 10.3 ml (7.31 g, 0.1 moles) of diethylamine is heated at 180° C. for 7 hours in a steel bomb. The mixture is allowed to cool, dissolved in 100 ml of diethyl ether, the solution is washed thrice with 20 ml of water, each, dried over anhydrous magnesium sulfate, and the solvent is evaporated under reduced pressure. The oily residue is distilled under reduced pressure. 2.7 g (57.8%) of an oily substance are obtained, which contains the two compounds mentioned in the title together with a minor amount of impurities. This crude mixture boils at 110°–120° C./66.7 Pa. The crude mixture is distilled again to obtain 1.8 g of a pure product boiling at 112°–114° C./66.7 Pa, which contains the two isomers in a ratio of about 1:3.

The starting substance, 1-(2,6-dimethylphenyl)-2-methyl-aziridine, is prepared as follows:

22.8 g (0.115 moles) of 1-(2,6-dimethylphenyl-amino)-2-chloro-propane, prepared as described in Step (a) of Example 11, are dissolved in 300 ml of ethanol. 50 ml of a 10 n aqueous sodium hydroxide solution are added, and the mixture is boiled for one hour. The mixture is allowed to cool, poured onto 500 ml of ice water, and the resulting mixture is extracted thrice with 100 ml of chloroform, each. The chloroform solutions are combined, washed thrice with 100 ml of water, each, dried over anhydrous magnesium sulfate, and the solvent is evaporated under reduced pressure. The oily residue is distilled under reduced pressure. 15.9 g (86.2%) of 1-(2,6-dimethylphenyl)-2-methyl-aziridine are obtained; b.p.: 70°–74° C./40 Pa.

Method C

A mixture of 5.2 g (28 mmoles) of 1-diethylamino-2-chloro-propane hydrochloride and 10.4 ml (10.2 g, 84 mmoles) of 2,6-dimethyl-aniline is heated at 140°–145° C. for 3 hours under nitrogen atmosphere. The mixture is allowed to cool and dissolved in a mixture of 60 ml of water and 30 ml of benzene. The two-phase mixture is rendered alkaline with concentrated aqueous ammonia under ice cooling. The phases are separated from each other, and the aqueous phase is extracted twice with 30 ml of benzene, each. The benzene solutions are combined, washed thrice with 30 ml of water, each, dried over anhydrous magnesium sulfate, and the solvent is evaporated under reduced pressure. The oily residue, weighing 9.7 g, is distilled under reduced pressure. Unreacted 2,6-dimethyl-aniline is obtained as the first fraction, b.p.: 62°–65° C./66.7 Pa, and then an isomeric mixture, containing the two title compounds in a ratio of about 3:10, is obtained as the second fraction. In this way 5.1 g (77.6%) of the isomeric mixture are obtained; b.p.: 116°–120° C./66.7 Pa.

Method D

One proceeds as described in Method (C) above, with the difference that 6.45 g (34.5 mmoles) of 2-diethylamino-1-chloro-propane hydrochloride and 13 ml (12.65 g, 104 mmoles) of 2,6-dimethylaniline are applied as starting substances. 4.9 g (60.5%) of an isomeric mixture, boiling at 122°–124° C./80 Pa, are obtained, which contains the two title compounds in a ratio of about 1:3.

EXAMPLE 15

Preparation of
1-amino-2-[N-methyl-N-(2,6-dimethylphenyl)-amino]-propane 2.5 ml of a 90% hydrazine hydrate are added to a solution of 3.0 g (9.3 mmoles) of 1-phthalimido-2-[N-methyl-N-(2,6-dimethylphenyl)-amino]-propane in 30 ml of ethanol, and the mixture is boiled for one hour. Next day the mixture is processed as described in Example 11, and the crude product is distilled under reduced pressure. 1.33 g (74.5%) of 1-amino-2-[N-methyl-N-(2,6-dimethylphenyl)-amino]-propane are obtained; b.p.: 97°–99° C./53.3 Pa. The monohydrochloride of the product, prepared as described in Example 1, melts at 158°–160° C.

The starting substance, 1-phthalimido-2-[N-methyl-N-(2,6-dimethylphenyl)-amino]-propane, is prepared as follows:

STEP A

Preparation of
1-[N-methyl-N-(2,6-dimethylphenyl)-amino]-2-propanol

A mixture of 35.5 g (0.26 moles) of N-methyl-2,6-dimethyl-aniline, 300 ml of water, 300 ml of ethanol and 21 ml (17.4 g, 0.3 moles) of 1,2-propylene-oxide is boiled for 3 hours. Ethanol is evaporated under reduced pressure, and the aqueous residue is extracted thrice with 100 ml of chloroform, each. The chloroform solutions are combined, dried over anhydrous magnesium sulfate, the solvent is evaporated, and the oily residue is subjected twice to fractional distillation. 18.4 g (51.8%) of N-methyl-2,6-dimethyl-aniline are recovered as the first fraction, boiling at 62° C./120 Pa, and then 8.1 g (33.4%, calculated for the converted starting substance) of 1-[N-methyl-N-(2,6-dimethylphenyl)-amino]-2-propanol are obtained; b.p.: 102°–106° C./120 Pa.

STEP B

Preparation of
1-[N-methyl-N-(2,6-dimethylphenyl)-amino]-2-chloro-propane 3.1 ml (4.6 g, 40 mmoles) of methanesulfonyl chloride are added dropwise, at a temperature not exceeding 20° C., to a solution of 7.0 g (36.2 mmoles) of 1-[N-methyl-N-(2,6-dimethylphenyl)-amino]-2-propanol and 5.45 ml (4.0 g, 40 mmoles) of triethyl amine in 50 ml of 1,2-dichloroethane, and the resulting mixture is stirred at room temperature for 3 hours. The mixture is washed then thrice with 30 ml of water, each, dried over anhydrous magnesium sulfate, the solvent is evaporated, and the oily residue is distilled under reduced pressure. 6.9 g (90.2%) of 1-[N-methyl-N-(2,6-dimethylphenyl)-amino]-2-chloro-propane are obtained; b.p.: 116°–118° C./133 Pa.

STEP C

Preparation of
1-phthalimido-2-[N-methyl-N-(2,6-dimethylphenyl)-amino]-propane and
1-[N-methyl-N-(2,6-dimethylphenyl)-amino]-2-phthalimido-propane A mixture of 6.9 g (32.6 mmoles) of 1-[N-methyl-N-(2,6-dimethylphenyl)-amino]-2-chloro-propane, prepared as described in Step (b), 50 ml of dry dimethyl formamide and 12.0 g (65 mmoles) of potassium phthalimide is stirred at 145°–150° C. for 2 hours. The mixture is cooled, poured onto ice water, and the aqueous mixture is extracted thrice with 80 ml of diethyl ether, each. The etheral solution is washed thrice with 30 ml of 1 n aqueous sodium hydroxide solution and thrice with 30 ml of water, each, dried over anhydrous magnesium sulfate, and the solvent is evaporated. The resulting yellow, syrup-like residue, weighing 7.0 g, is dissolved in 10 ml of diisopropyl ether, and the solution is maintained at +5° C. for one week. 3.22 g (30.7%) of a yellow, crystalline substance are obtained; m.p.: 70°–72° C. Based on the NMR spectrum, this substance is 1- phthalimido-2-[N-methyl-N-(2,6-dimethylphenyl)-amino]-propane.

Diisopropyl ether is evaporated from the mother liquor under reduced pressure, and the oily residue is purified by chromatography on 200 g of silica gel. A 8:1 mixture of benzene and ethyl acetate is applied as eluant. 3.4 g (32.4%) of a yellow, honey-like substance are obtained; this product is an about 2:5 mixture of 1-phthalimido-2-[N-methyl-N-(2,6-dimethylphenyl)-amino]-propane and 1-[N-methyl-N-(2,6-dimethylphenyl)-amino]-2-phthalimido-propane. The total yield obtained in Step (c) is 63.1%.

EXAMPLE 16

Preparation of 1-[N-(2,6-dimethylphenyl)-methane-sulfonamido]-2-diethylamino-propane A mixture of 15 g (45 mmoles) of 1-[N-(2,6-dimethylphenyl)-methanesulfonamido]-2-methanesulfonyloxy-propane and 45 ml (31.9 g, 0.44 moles) of diethyl amine is heated at 150° C. for 5 hours in a steel bomb. The mixture is cooled, dissolved in 300 ml of diethyl ether, the solution is washed thrice with 50 ml of water, each, and then extracted thrice with 70 ml of ice-cold 1 n hydrochloric acid, each. The acidic solutions are combined, the traces of diethyl ether are removed under reduced pressure, and then the pH of the solution is adjusted to 9 with concentrated aqueous ammonia. The mixture is allowed to stand at +5° C. for one hour. The separated crystalline substance is filtered off, washed with water and dried. 8.3 g (59.1%) of 1-[N-(2,6-dimethylphenyl)-methanesulfonamido]-2-diethylamino-propane are obtained as a light beige, crystalline substance; m.p.: 58°–60° C.

The starting substance, 1-[N-(2,6-dimethylphenyl)-methanesulfonamido]-2-methanesulfonyloxy-propane, is prepared as follows:

METHOD A

Step A

Preparation of 1-[N-(2,6-dimethylphenyl)-methane-sulfonamido]-2-propanol 20 g (0.1 moles) of N-(2,6-dimethylphenyl)-methane-sulfonamide, prepared as described by M. A. Bambenek [Rec. Trav. Chim. 82, 97 (1963)] for the corresponding p-toluenesulfonamide derivative, m.p.: 128°–129° C., are dissolved in 200 ml of 0.5 n aqueous sodium hydroxide solution under stirring. 12.7 ml (10.6 g, 0.18 moles) of 1,2-propylene-oxide are added dropwise to the solution at 80°–85° C. within 3 hours, and then the mixture is allowed to stand overnight. The separated crystalline substance is filtered off, washed with water and dried. 19.4 g (75.5%) of 1-[N-(2,6-dimethylphenyl)-methane-sulfonamido]-2-propanol are obtained; m.p.: 81°–84° C. When recrystallized from diisopropyl ether, the product melts at 85°–87° C.

The aqueous filtrate is extracted thrice with 50 ml of diethyl ether, each, the etheral solution is dried over anhydrous magnesium sulfate, and the solvent is evaporated under reduced pressure. Additional 1.7 g of the required product are obtained, thus the total yield is 83%.

1-[N-(2,6-dimethylphenyl)-methanesulfonamido]-2-propanol can also be prepared so that 1-chloro-2-propanol is substituted for 1,2-propylene-oxide in the above reaction. The product is obtained with a yield of 70%. Similarly can be prepared 1-[N-(2,6-dimethylphenyl)-p-toluenesulfonamido]-2-propanol; m.p.: 114°–115° C.

STEP B

Preparation of 1-[N-(2,6-dimethylphenyl)-methanesulfonamido]-2-methanesulfonyloxy-propane 31.4 ml (46.6 g, 0.4 moles) of methanesulfonyl chloride are added dropwise, within one hour, to a solution of 94.5 g (0.368 moles) of 1-[N-(2,6-dimethylphenyl)-methane-sulfonamido]-2-propanol and 55.3 ml (40.5 g, 0.4 moles) of trietyl amine in 600 ml of 1,2-dichloroethane. During the addition the mixture is cooled with ice to maintain its temperature at 10°–12° C. The mixture is stirred at room temperature for additional 4 hours and then washed thrice with 100 ml of water, each. The dichloroethane solution is dried over anhydrous magnesium sulfate, the solvent is evaporated under reduced pressure, and the thick, oily residue is triturated with 120 ml of isopropanol. The resulting crystals are filtered off, washed with ice-cold isopropanol and dried. 93.2 g (75.8%) of 1-[N-(2,6-dimethylphenyl)-methane-sulfonamido]-2-methanesulfonyloxy-propane are obtained as a white, crystalline substance melting at 111°–114° C.

METHOD B 1.0 g of a 80% mineral oil dispersion of sodium hydride is added in small portions, at room temperature, to a mixture of 6.0 g (30 mmoles) of N-(2,6-dimethylphenyl)-methanesulfonamide and 100 ml of dry toluene, and the resulting mixture is heated to 100° C. within 0.5 hours. 7.0 g (30 mmoles) of 1,2-bis(methanesulfonyloxy)-propane are added to the mixture at 100°–105° C. within one hour, and the reaction mixture is stirred at the same temperature for 5 hours. The mixture is cooled, washed thrice with 20 ml of water, twice with 25 ml of 1 n aqueous sodium hydroxide solution and then thrice with 30 ml of water, each, dried over anhydrous magnesium sulfate, and the solvent is evaporated under reduced pressure. The resulting oily substance, weighing 5.9 g, is triturated with diethyl ether to obtain 4.4 g (44%) of a crude, solid product, m.p.: 70°–80° C. The crude product is recrystallized twice from isopropanol to obtain 1.85 g (18.5%) of 1-[N-(2,6-dimethylphenyl)-methanesulfonamido]-2-methanesulfonyloxy-propane, m.p.: 117°–120° C. This compound is identical with the product obtained according to Method (A).

EXAMPLES 17 to 20

Compounds of the general formula (I) in which $R^1$, $R^2$ and $R^5$ represent methyl group, $R^3$ is methanesulfonyl group, $R^4$ is hydrogen and n is zero, whereas $R^6$ and $R^7$ are as given in Table 12, are prepared using the appropriate amines as described in Example 16.

TABLE 12

| Example No. | $R^6$ | $R^7$ | M.p. °C. |
|---|---|---|---|
| 17 | $CH_3$ | H | 251–253* |
| 18 | $CH_3$ | $CH_3$ | 238–240* |
| 19 | $NR^6R^7$ = 1-piperazinyl | | 204–205** |
| 20 | $CH(CH_3)_2$ | H | 58–60 (base) |

*Hydrochloride
**Dihydrochloride

EXAMPLE 21

Preparation of 1-[N-(2,6-dimethylphenyl)-methane-sulfonamido]-2-amino-propane

Method A 16.5 ml of a 98% hydrazine hydrate are added to a solution of 22.0 g (57 mmoles) of 1-[N-(2,6-dimethylphenyl)-methanesulfonamido]-2-phthalimido-propane in 500 ml of ethanol at about 70° C., and the resulting mixture is boiled for one hour. Next day the separated phthalyl hydrazide is filtered off, and the solvent is evaporated from the filtrate under reduced pressure. The crude, oily residue crystallizes upon scratching 14.6 g (100%) of 1-[N-(2,6-dimethylphenyl)-methanesulfonamido]-2-amino-propane are obtained as an almost colourless, crystalline substance; m.p.: 106°–109° C.

The starting substance, 1-[N-(2,6-dimethylphenyl)-methanesulfonamido]-2-phthalimido-propane, is prepared as follows:

33.3 g/0.19 moles of potassium phthalimide are added to a solution of 30 g (89 mmoles) of 1-[N-(2,6-dimethylphenyl)-methane-sulfonamido]-2-methanesulfonyloxy-propane in 300 ml of dry dimethyl formamide, and the mixture is stirred at 145°–150° C. for one hour. The mixture is cooled, poured onto 800 ml of ice water, and the aqueous mixture is extracted thrice with 200 ml of chloroform, each. The chloroform solution is washed thrice with 50 ml of n sodium hydroxide solution and then thrice with 100 ml of water, each, dried over anhydrous magnesium sulfate, and the solvent is evaporated under reduced pressure. The oily residue is triturated with 35 ml of isopropanol, the separated crystalline substance is filtered off, washed with ice-cold isopropanol and dried. 22 g (64.1%) of 1-[N-(2,6-dimethylphenyl)-methanesulfonamido]-2-phthalimido-propane are obtained as a colourless, crystalline substance; m.p.: 124°–127° C.

METHOD B

A mixture of 1.0 g (3 mmoles) of 1-[N-(2,6-dimethylphenyl)-methanesulfonamido]-2-methanesulfonyloxy-propane, 10 ml of methanol and 5 ml of concentrated aqueous ammonia is heated at 110° C. for 6 hours in a steel bomb. The mixture is cooled, diluted with 30 ml of water, and methanol is evaporated under reduced pressure. The residue is extracted thrice with 20 ml of chloroform, each. The chloroform solutions are combined, washed thrice with 20 ml of water, each, dried over anhydrous magnesium sulfate, and the solvent is evaporated under reduced pressure. The residue is triturated with 3 ml of diisopropyl ether. 0.55 g of 1-[N-(2,6-dimethylphenyl)-methanesulfonamido]-2-amino-propane are obtained; m.p.: 106°–109° C.

EXAMPLES 22 to 24

Compounds of the general formula (I) in which $R^3$ is methanesulfonyl group, $R^6$ and $R^7$ stand for hydrogen and $R^1$, $R^2$, $R^4$, $R^5$ and n are as given in Table 13 are prepared from the appropriately substituted starting substances according to Method (A) of Example 21.

TABLE 13

| Example No. | $R^1$ | $R^2$ | $R^4$ | $R^5$ | n | M.P. °C. |
|---|---|---|---|---|---|---|
| 22 | CH₃ | CH₃ | CH₃ | H | 0 | 43–45 |
| 23 | CH₃ | CH₃ | H | CH₃ | 1 | (90%) oil |
|    | CH₃ | CH₃ | CH₃ | H | 1 | (10%) |
| 24 | C₂H₅ | C₂H₅ | H | CH₃ | 0 | 47–49 |

The physcial constants of the intermediates used in the preparation of the product of Example 24 are listed in Table 14.

TABLE 14

| Intermediate | M.p. °C. |
|---|---|
| N-(2,6-Diethylphenyl)-methanesulfonamide* | 66–69 |
| 1-[N-(2,6-Diethylphenyl)-methanesulfonamido]-2-propanol* | 129–133 |
| 1-[N-(2,6-Diethylphenyl)-methanesulfonamido]-2-methanesulfonyloxy-propane* | 76–78 |
| 1-[N-(2,6-Diethylphenyl)-methanesulfonamido]-2-phthalimido-propane** | 106–109 |

Remarks:
*These intermediates are prepared as the respective homologues mentioned in Example 16.
**This intermediate is prepared according to the method described in Example 21 for the preparation of the starting substance.

Remarks: *These intermediates are prepared as the respective homologues mentioned in Example 16. **This intermediate is prepared according to the method described in Example 21 for the preparation of the starting substance.

EXAMPLE 25

Preparation of 1-phthalimido-2-[N-(2,6-dimethylphenyl)-methanesulfonamido]-propane

Method A 45.3 g (0.164 moles) of 1-chloro-2-[N-(2,6-dimethylphenyl)-methanesulfonamido]-propane are dissolved in 700 ml of dry dimethyl formamide, 61 g (0.33 moles) of potassium phthalimide and 1 g (6 mmoles) of potassium iodide are added, and the mixture is stirred at 140°–145° C. for 7 hours. The reaction mixture is processed as described in Example 21 for the preparation of the starting substance. The resulting 46.6 g of crude, honey-like substance is triturated with 50 ml of diethyl ether, the separated crystalline substance is filtered off, washed with diethyl ether and dried. 23.05 g of a crystalline substance are obtained; m.p.: 155°–160° C. This substance is purified further by stirring it with 50 ml of diethyl ether at room temperature. Thereafter the crystals are filtered off, washed with diethyl ether and dried. 16.75 g (26.4%) of 1-phthalimido-2-[N-(2,6-dimethylphenyl)-methanesulfonamido]-propane are obtained; m.p.: 188°–190° C.

The etheral mother liquors are concentrated, and the separated solids are filtered off. 10.6 g (27%) of 2-[N-(2,6-dimethylphenyl)-methanesulfonamido]-1-propene are obtained; m.p.: 80°–81° C.

The starting substance, 1-chloro-2-[N-(2,6-dimethylphenyl)-methanesulfonamido]-propane, is prepared as follows:

5.2 g of a 80% mineral oil dispersion of sodium hydride are added in small portions, at room temperature, to a suspension of 31.5 g (0.158 moles) of N-(2,6-dimethylphenyl)-methanesulfonamide in 400 ml of dry toluene. The resulting mixture is heated slowly, within about one hour, to 100° C., and then 27.3 g (0.158 moles) of 1-chloro-2-methanesulfonyloxy-propane are added dropwise to the mixture at the same temperature within 0.5 hours. The reaction mixture is stirred at 100°–110° C. for 12 hours, thereafter it is cooled, placed into an ice bath, and 100 ml of water are introduced dropwise. The aqueous phase is separated, the toluene phase is washed with 100 ml of water, twice with 100 ml of 1 n aqueous sodium hydroxide and finally with 100 ml of water, dried over anhydrous magnesium sulfate, and the solvent is evaporated under reduced pressure. The thick, yellow, oily residue, weighing 33.9 g, is distilled under reduced pressure. 26.15 g of 1-chloro-2-[N-(2,6-dimethylphenyl)-methanesulfonamido]-propane are obtained as a slightly opalescent oil; b.p.: 150°–154° C./26.6 Pa.

The aqueous and the alkaline washes are combined and acidfied with 20% hydrochloric acid to pH 2.1.1.4 g of unreacted N-(2,6-dimethylphenyl)-methanesulfonamide are recovered; m.p.: 126°–128° C. Thus the 1-chloropropane compound is obtained with a yield of 94% calculated for the converted starting substance.

METHOD B 0.15 g of a 80% mineral oil dispersion of sodium hydride are added in some portions to a solution of 1.0 g (5 mmoles) of N-(2,6-dimethylphenyl)-methanesulfonamide in 20 ml of dry toluene, and the mixture is heated to 100°–105° C. within one hour. A solution of 1.4 g (5 mmoles) of N-(β-methanesulfonyloxy-propyl)-phthalimide in 15 ml of toluene is added dropwise to the mixture within 0.5 hours at the same temperature, and the mixture is stirred then at 100°–105° C. for 10 hours. The mixture is cooled, 20 ml of water are added dropwise to it, thereafter the toluene phase is separated, washed twice with 10 ml of 1 n aqueous sodium hydroxide solution and thrice with 20 ml of water, each, dried over anhydrous magnesium sulfate, and the solvent is evaporated under reduced pressure. The solid residue is triturated with dry diethyl ether. 0.46 g (23.8%) of crude 1-phthalimido-2-[N-(2,6-dimethylphenyl)-methanesulfonamido]-propane are obtained. The crude product is stirred at room temperature in 100 ml of diethyl ether for one hour to obtain a purified product melting at 196°–198° C.

N-(β-methanesulfonyloxy-propyl)-phthalimide, used as starting substance, is prepared as follows:

5.55 g (30 mmoles) of potassium phthalimide are added in small portions, within 1 hour, to a solution of 7.0 g (30 mmoles) of 1,2-bis(methanesulfonyloxy)-propane in 70 ml of dry dimethyl formamide, heated to 100°–105° C. The mixture is stirred at the same temperature for additional 0.5 hours, thereafter it is cooled and poured onto 350 ml of ice water. The separated crystalline substance is filtered off, washed with water and dried. This crude product, weighing 4.36 g (m.p.: 111°–121° C.) is recrystallized from 25 ml of isopropanol to obtain 3.53 g (41.5%) of N-(β-methanesulfonyloxy-propyl)-phthalimide; m.p.: 129°–132° C.

EXAMPLE 26

Preparation of a mixture of
1-[N-(2,6-dimethylphenyl)-methanesulfonamido]-3-phthalimido-butane and
1-phthalimido-3-[N-(2,6-dimethylphenyl)-methanesulfonamido]-butane 18 g (90 mmoles) of N-(2,6-dimethylphenyl)-methane-sulfonamide are dissolved in 200 ml of a 0.5 n aqueous sodium hydroxide solution, and 14.4 ml (26 g, 0.12 moles) of 1,3-dibromo-propane are added dropwise, within 4 hours, to the stirred solution at 90°–95° C. The mixture is stirred for one additional hour at the same temperature, thereafter it is allowed to cool and extracted thrice with 80 ml of benzene, each. The benzene solutions are combined, washed twice with 100 ml of a 1 n aqueous sodium hydroxide solution and then thrice with 100 ml of water, each, dried over sodium sulfate, and the solvent is evaporated under reduced pressure. The oily intermediate, weighing 14.6 g, is reacted further without purification.

A mixture of the oily intermediate obtained as described above, 200 ml of dry dimethyl formamide and 16.3 g (88 mmoles) of potassium phthalimide is stirred at 60°–65° C. for one hour. The mixture is cooled, poured onto one litre of ice water, and allowed to stand for about 15 hours. The separated crystalline substance is filtered off, washed with water, dried, and the resulting crude substance, weighing 12 g, is stirred in 30 ml of isopropanol at room temperature for 0.5 hours. The crystalline product is filtered off, washed with ice-cold isopropanol and dried. 7.95 g (49.5%) of a product melting at 145°–150° C. are obtained. This product is an about 90:10 mixture of 1-[N-(2,6-dimethylphenyl)-methanesulfonamido]-3-phthalimido-butane and 1-phthalimido-3-[N-(2,6-dimethylphenyl)-methanesulfonamido]-butane.

EXAMPLE 27

Preparation of
1-(2,6-dimethylphenyl-amino)-2-amino-propane and
1-amino-2-(2,6-dimethylphenyl-amino)-propane

METHOD A 0.42 g (30 mmoles) of o-chloro-benzaldehyde are admixed with 0.5 g (28 mmoles) of an about 2:5 mixture of the two title compounds, prepared as described in Example 11, and the mixture is allowed to stand at +5° C. for 24 hours. The mixture is dissolved in 20 ml of diethyl ether, the solution is dried over anhydrous magnesium sulfate, and the solvent is evaporated. The resulting mixture of isomeric Schiff-bases is subjected to preparative thin layer chromatography in order to separate the individual isomers. A silica gel plate prepared with a 2% aqueous sodium hydrocarbonate solution is applied as adsorbent, and a 2:1 mixture of petroleum ether (b.p.: 40°–100° C.) and diethyl ether is utilized as eluant. The following substances are obtained:

1-(2,6-dimethylphenyl-amino)-2-(o-chloro-benzylideneamino)-propane; $R_f$=0.4, and 1-(o-chloro-benzylideneamino)-2-(2,6-dimethylphenyl-amino)-propane; $R_f$=0.5.

The separated isomers are treated in ethanolic solution, at room temperature, with a 20% aqueous hydrochloric acid solution to obtain the pure amino compounds.

METHOD B 2.0 g (11.2 mmoles) of an about 2:5 mixture of the two title compounds, prepared as described in Example 11, are dissolved in 40 ml of 1,2-dichloroethane, and 1.6 ml (1.17 g, 11.6 mmoles) of triethyl amine are added. The mixture is cooled to +5° C., and 2.1 g (11.1 mmoles) of p-toluenesulfonic acid chloride are added in small portions, within about 20 minutes. The reaction mixture is stirred at 5°–10° C. for additional 2 hours, thereafter washed thrice with 30 ml of water, each, dried over anhydrous magnesium sulfate, and the solvent is evaporated under reduced pressure. 5 ml of diethyl ether are added to the colourless, honey-like residue weighing 3.32 g, and the mixture is allowed to stand overnight. The separated colourless, crystalline substance is filtered off, washed with diethyl ether and dried. 2.0 g (76.2%, calculated for the respective isomer of the starting amine mixture) of 1-(p-toluenesulfonamido)-2-(2,6-dimethylphenyl-amino)-propane are obtained; m.p.: 83°–84° C. The product melts at 85° C. after recrystallization from isopropanol.

The etheral mother liquor obtained in the previous step is evaporated, and the residue is purified by chromatography on 70 g of silica gel. A 8:1 mixture of benzene and ethyl acetate is applied as eluant. The fractions which contain a substance with an $R_f$ value of 0.37 are combined, the solvent is evaporated, and the oily residue, weighing 0.8 g, is triturated with 3 ml of diisopropyl ether to effect crystallization. 0.28 g (26.7%, calculated for the respective isomer of the starting amine mixture) of 1-(2,6-dimethylphenyl-amino)-2-(p-toluenesulfonamido)-propane are obtained; m.p.: 80°–81° C.

The diisopropyl ether mother liquor obtained in the previous step is partially evaporated, and the concentrate is allowed to stand for some days. In this way 0.15 g (14.3%) of an isomeric mixture are obtained; this product contains 1-(2,6-dimethylphenyl-amino)-2-(p-toluenesulfonamido)-propane and 1-(p-toluenesulfonamido)-2-(2,6-dimethylphenyl-amino)-propane in a ratio of about 5:2.

The individual p-toluenesulfonyl derivatives are deprotected then as described in Example 1 to obtain 1-(2,6-dimethylphenyl)-amino-2-amino-propane and 1-amino-2-(2,6-dimethylphenyl-amino)-propane as pure isomers.

EXAMPLE 28

Preparation of
1-phthalimido-2-(2,6-dimethylphenyl-amino)-propane

A mixture of 1.24 ml (1.21 g, 10 mmoles) of 2,6-dimethyl-aniline and 1.4 g (5 mmoles) of N-(β-methanesulfonyloxy-propyl)-phthalimide is maintained at 160°–165° C. for 2 hours under nitrogen atmosphere. The mixture is cooled, dissolved in 20 ml of chloroform, the solution is washed thrice with 10 ml of 1 n aqueous hydrochloric acid and thrice with 10 ml of water, each, dried over anhydrous magnesium sulfate, and the solvent is evaporated under reduced pressure. The dark yellow, thick, oily residue, weighing 1.5 g, is triturated with 1.5 ml of isopropanol to obtain 0.53 g (38%) of unreacted N-(β-methanesulfonyloxy-propyl)-phthalimide as a crystalline substance. The crystals are filtered off, and the filtrate is allowed to stand for some days. 0.34 g (35.4%, calculated for the converted phthalimide derivative) of 1-phthalimido-2-(2,6-dimethylphenyl-amino)-propane are obtained as colourless needles; m.p.: 102°–103° C.

This compound can be converted into 1-amino-2-(2,6-dimethylphenyl-amino)-propane (b.p.: 108°–110° C./53.3 Pa) as described in Example 11.

EXAMPLE 29

Preparation of
1-(2,6-dimethylphenyl-amino)-2-amino-butane 2.5 g (66 mmoles) of lithium-aluminium-hydride are added in small portions, at room temperature, to a solution of 3.6 g (17.4 mmoles) of N-(2-aminobutyryl)-2,6-dimethyl-aniline in 40 ml of dry diethyl ether, and the resulting mixture is boiled for 3 hours. The mixture is cooled with ice, and 10 ml of ethyl acetate, 10 ml of water, finally 12 ml of a 5 n aqueous sodium hydroxide solution are added dropwise. The etheral phase is decanted, and the thick, gelly aqueous phase is washed thrice with 25 ml of diethyl ether, each. The etheral solutions are combined, washed thrice with 25 ml of water, each, dried over anhydrous magnesium sulfate, and the solvent is evaporated. The yellow, oily residue is distilled under reduced pressure to obtain 1.37 g of 1-(2,6-dimethylphenyl-amino)-2-amino-butane, b.p.: 122°–124° C./66.7 Pa, and 0.62 g of unreacted starting substance, b.p.: 158°–172° C./66.7 Pa. The product is obtained with a yield of 49%, calculated for the converted starting substance.

The product is converted into its hydrochloride as described in Example 1. The salt melts at 240°–241° C. after recrystallization from isopropanol.

The starting substance, N-(2-amino-butyryl)-2,6-dimethyl-aniline, can be prepared according to the method of E. W. Byrnes et al. [J. Med. Chem. 22, 1171 (1979)]. A further method for the preparation of the starting substance is described bellow.

STEP A

Preparation of
N-(2-bromo-butyryl)-2,6-dimethyl-aniline

A solution of 85 g (0.37 moles) of α-bromobutyryl bromide in 100 ml of benzene is added dropwise, within 0.5 hours, to a solution of 100 ml (102.3 g, 0.845 moles) of 2,6-dimethyl-aniline in 500 ml of dry benzene. The mixture is cooled with water to maintain its temperature at 25° C. during addition. Thereafter the mixture is stirred at room temperature for 4 hours. The precipitate is filtered off, washed with benzene, and dried. The filtrate is washed thrice with 100 ml of water, thrice with 200 ml of 1 n hydrochloric acid and then again thrice with 200 ml of water, each, dried over anhydrous magnesium sulfate, and the solvent is evaporated under reduced pressure. The solid residue is triturated with diethyl ether to obtain 12.8 g of the crude product.

The precipitate obtained in the previous step is stirred in 500 ml of 1,2-dichloroethane at room temperature for one hour, and then the insoluble 2,6-dimethyl-aniline hydrobromide is filtered off. The dichloroethane filtrate is washed with water, aqueous hydrochloric acid and water as described above, dried over anhydrous magnesium sulfate, and concentrated then to a final volume of about 100 ml. 27.2 g of pure N-(2-bromo-butyryl)-2,6-dimethyl-aniline separates from the concentrate as a crystalline substance; m.p.: 180°–190° C. (fraction "A"). The dichloroethane filtrate is concentrated further to obtain 5.35 g of a somewhat contaminated product. This fraction is combined with the crude product separated from the benzene solution as described above and recrystallized from 12 ml of 1,2-dichloroethane. 6.41 g of pure N-(2-bromo-butyryl)-2,6-dimethyl-aniline (fraction "B") are obtained; m.p.: 175°–190° C. The total yield (fractions "A"+"B") is 33.3%.

STEP B

Preparation of
N-(2-phthalimido-butyryl)-2,6-dimethyl-aniline

A mixture of 20.0 g (74 mmoles) of N-(2-bromo-butyryl)--2,6-dimethyl-aniline, 27.8 g (0.15 moles) of potassium phthalimide and 150 ml of dry dimethyl formamide is stirred at 60° C. for 2 hours. The mixture is cooled, poured onto 750 ml of ice water, the separated crystalline substance is filtered off, washed with water and dried. The resulting crude product, weighing 35.7 g, is dissolved in 200 ml of chloroform, the solution is washed thrice with 50 ml of 1 n aqueous sodium hydroxide solution and thrice with 50 ml of water, each, dried over anhydrous magnesium sulfate, and the solvent is evaporated under reduced pressure. 17.7 g (71.1%) of N-(2-phthalimido-butyryl)-2,6-dimethyl-aniline are obtained; m.p.: 195°–196° C.

STEP C

Preparation of
N-(2-amino-butyryl)-2,6-dimethyl-aniline

A mixture of 17.7 g (52.6 mmoles) of N-(2-phthalimido-butyryl)-2,6-dimethyl-aniline, 14.2 ml of a 85% aqueous hydrazine hydrate solution and 250 ml of ethanol is boiled for one hour, and then the mixture is processed as described in Example 11. The product is triturated with petroleum ether. 9.45 g of N-(2-amino-butyryl)-2,6-dimethyl-aniline are obtained; m.p.: 48°–49° C. The product is obtained with a yield of 87.1%. The hydrochloride of the compound melts at 213°–214° C. [the melting point reported in the literature (see E. W. Byrnes et al., loc. cit.) is 213.5°–214.5° C.].

EXAMPLE 30

Preparation of
1-(2,6-dimethylphenyl-amino)-2-dimethylamino-butane

One proceeds as described in Example 29 with the difference that N-(2-dimethylamino-butyryl)-2,6-dimethyl-aniline is applied as starting substance. The title compound is obtained with a yield of 61%; b.p.: 125°–127° C./113 Pa. The dihydrochloride of the product melts at 158°–160° C.

The starting substance, N-(2-dimethylamino-butyryl)-2,6-dimethyl-aniline, can be prepared as follows:

A mixture of 7.7 g (28.5 mmoles) of N-(2-bromo-butyryl)-2,6-dimethyl-aniline, 70 ml of ethanol and 20 ml of a 33% aqueous dimethyl amine solution is heated in a bomb at 100°–110° C. for 6 hours. The mixture is cooled, diluted with 150 ml of diethyl ether and 40 ml of water, the phases are separated, and the aqueous phase is extracted twice with 25 ml of diethyl ether, each. The etheral solutions are combined, washed thrice with 35 ml of 1 n aqueous hydrochloric acid, each, the aqueous acidic solutions are combined, rendered alkaline (pH=9) with concentrated aqueous ammonia, and extracted thrice with 40 ml of 1,2-dichloroethane, each. The dichloroethane solutions are combined, washed thrice with 20 ml of water, each, dried over anhydrous magnesium sulfate, and the solvent is evaporated under reduced pressure. The oily residue, weighing 7.1 g, is triturated with diisopropyl ether to obtain 4.1 g of crude product, which is recrystallized then from ethyl acetate. 3.2 g (47.9%) of pure N-(2-dimethylamino-butyryl)-2,6-dimethyl-aniline are obtained; m.p.: 155°–157° C.

EXAMPLE 31

Preparation of
1-[N-(2,6-dimethylphenyl)-benzamido]--2-diethylamino-propane

A mixture of 6.0 g (20 mmoles) of 1-[N-(2,6-dimethylphenyl)-benzamido]-2-chloro-propane and 10.3 ml (7.3 g, 0.1 mole) of diethyl amine is heated at 160° C. for 12 hours in a steel bomb. The mixture is cooled and processed as described in Example 16. The resulting oily crude base, weighing 5.0 g, is dissolved in 30 ml of diisopropyl ether, the solution is allowed to stand for one day, and then the insolubles are filtered off. The filtrate is evaporated under reduced pressure. 4.35 g (64%) of 1-[N-(2,6-dimethylphenyl)-benzamido]-2-diethylamino-propane are obtained as a yellow oil.

1-[N-(2,6-Dimethyl-phenyl)-toluenesulfonamido]-2-dimethylamino-propane can be prepared in a similar way.

0.5 g of 1-[N-(2,6-dimethylphenyl)-benzamido]-2-diethylamino-propane are dissolved in 2 ml of isopropanol, 1 ml of a 10 w/v % isopropanolic hydrochloric acid solution is added to it, and the solvent is evaporated under reduced pressure. The residue is triturated with 5 ml of ethyl acetate to effect crystallization. The resulting hydrochloride melts at 173°–174° C.

The starting substance, 1-[N-(2,6-dimethylphenyl)-benzamido]-2-chloro-propane, is prepared as follows:

STEP A

Preparation of
1-[N-(2,6-dimethylphenyl)-benzamido]-2-propanol 100 ml of a 2 n aqueous sodium hydroxide solution are added dropwise, under ice cooling and vigorous stirring, to a suspension of 21.6 g (0.1 moles) of 1-(2,6-dimethylphenyl-amino)-2-propanol hydrochloride in 100 ml of benzene, and then 12.2 ml (14.6 g, 0.1 moles) of benzoyl chloride are dropped into the mixture at room temperature. The resulting mixture is stirred at room temperature for 5 hours and allowed to stand overnight. The aqueous phase is separated, the benzene phase is washed twice with 50 ml of water, twice with 50 ml of a 1 n hydrochloric acid solution and then thrice with 50 ml of water, each, dried over anhydrous magnesium sulfate, and the solvent is evaporated under reduced pressure. 26.6 g (94%) of 1-[N-(2,6-dimethylphenyl)-benzamido]-2-propanol are obtained as a white, crystalline substance; m.p.: 121°–122° C.

STEP B

Preparation of
1-[N-(2,6-dimethylphenyl)-benzamido]-2-chloro-propane 4.65 ml (7.7 g, 65 mmoles) of thionyl chloride are added dropwise, at room temperature, to a solution of 14.2 g (50 mmoles) of 1-[N-(2,6-dimethylphenyl)-benzamido]-2-propanol in 100 ml of dry benzene, and the mixture is boiled then for 45 minutes. The solvent is evaporated under reduced pressure, and 30 ml of benzene is distilled off from the residue in order to remove the traces of thionyl chloride. This latter operation is repeated. The solid residue is triturated with n-hexane, the crystalline product is filtered off, washed with n-hexane and dried. 14.3 g (95%) of 1-[N-(2,6-dimethylphenyl)-benzamido]-2-chloro-propane are obtained as a white, crystalline substance; m.p.: 106°–109° C.

EXAMPLE 32

Preparation of
1-ethylamino-2-(2,6-dimethylphenyl-amino)-propane

A mixture of 0.3 g (1.2 mmoles) of 1-(N-ethyl-acetamido)-2-(2,6-dimethylphenyl-amino)-propane and 5 ml of a 20% aqueous hydrochloric acid solution is boiled for 3 hours. The solvent is evaporated, and the residue is dissolved in 30 ml of water. The solution is washed five times with 5 ml of chloroform, each, and then the solvent is evaporated. The residue is crystallized from a mixture of chloroform and diethyl ether to obtain 0.14 g (56%) of 1-ethylamino-2-(2,6-dimethyl-phenyl-amino)-propane dihydrochloride; m.p.: 155°–157° C.

The starting substance, 1-(N-ethyl-acetamido)-2-(2,6-dimethylphenyl-amino)-propane is prepared as follows:

1-Ethylamino-2-propanol is diacetylated according to the method of W. J. Bailey and C. N. Bird [J. Org. Chem. 23, 996 (1958)], and then the ester group of the product is hydrolyzed to free hydroxy group in a 10% ethanolic potassium hydroxide solution at room temperature. The resulting 1-(N-ethyl-acetamido)-2-propanol, bp.: 100°–110° C./53.3 Pa, is chlorinated as described in Step b) of Example 31 under boiling the mixture for 3 hours, and the resulting 1-(N-ethylacetamido)-2-chloropropane, b.p.: 102°–110° C./53.3 Pa (6.0 g, 36.7 mmoles), is reacted with 9.3 ml (9.1 g, 75 mmoles) of 2,6-dimethyl-aniline for 3 hours at 140°–145° C. under nitrogen atmosphere with stirring. The mixture is cooled, dissolved in 40 ml of a 10% aqueous hydrochloric acid solution, and the solution is rendered alkaline (pH=9) with concentrated aqueous ammonia. The alkaline mixture is extracted thrice with 30 ml of chloroform, each. The chloroform solutions are combined, washed thrice with 30 ml of water, each, dried over magnesium sulfate, and the solvent is evaporated. The oily residue is distilled under reduced pressure. First the excess of 2,6-dimethyl-aniline is recovered (4.6 g, 98% of the excess; b.p.: 52°–62° C./53.3 Pa), and then the crude 1-(N-ethyl-acetamido)-2-(2,6-dimethylphenyl-amino)-propane distils at 120°–140° C./53.3 Pa. The resulting crude product, weighing 1.9 g (21%), is purified by chromatography on 80 g of silica gel; a 1:2 mixture of benzene and ethyl acetate is applied as eluant. A pure product, melting at 58°–60° C., is obtained.

EXAMPLE 33

Preparation of 1-diethylamino-2-(2,6-dimethylphenyl-amino)-propane

A solution of 0.2 g (0.8 mmoles) of 1-(N-ethyl-acetamido)-2(2,6-dimethylphenyl-amino)-propane, prepared as described in Example 31, in 5 ml of dry diethyl ether is added dropwise, within 10 minutes, to a vigorously stirred suspension of 0.2 g of lithium aluminium hydride in 10 ml of dry diethyl ether at room temperature. The resulting mixture is stirred at room temperature for 3 hours and then processed as described in Example 29. 0.14 g (74%) of 1-diethylamino-2-(2,6-dimethylphenyl-amino)-propane are obtained.

EXAMPLE 34

Preparation of 1-(N-methylformamido)-2-(2,6-dimethylphenyl-amino)-propane

One proceeds as described in Method C) of Example 14 with the difference that 2,6-dimethyl-aniline and 1-(N-methylformamido)-2-chloro-propane are applied as starting substances. The title compound is obtained with a yield of 22%; b.p.: 155°–165° C./80 Pa, m.p.: 69.5°–72° C.

EXAMPLE 35

Preparation of 1-(2-chloro-6-methyl-phenyl-amino)-2-dimethylamino-propane and 1-dimethylamino-2-(2-chloro-6-methyl-phenyl-amino)-propane A mixture of 10.1 g (46.3 mmoles) of 1-(2-chloro-6-methyl-phenyl-amino)-2-chloro-propane, 100 ml of ethanol and 32 ml of a 33% aqueous dimethylamine solution is heated at 180° C. for 6 hours in a bomb as described in Example 14, Method A). 7.6 g of the end-product are obtained; the product is an about 1:4 mixture of the two title compounds. Yield: 72%; b.p.: 108°–110° C./53.3 Pa.

7.4 g of the isomeric mixture obtained as described above are dissolved in 100 ml of ethyl acetate, and 12 ml of a 11 w/v % isopropanolic hydrochloric acid solution are added. The solution is allowed to stand for 2 days. 3.9 g of pure 1-dimethylamino-2-(2-chloro-6-methyl-phenyl-amino)-propane separate from the solution as a crystalline substance; m.p.: 148°–150° C.

The solvent is evaporated from the filtrate under reduced pressure, and the residue is subjected to chromatography as described in Method (A) of Example 14 to obtain the two title compounds in pure state.

EXAMPLE 36

Preparation of 1-(2,6-dichlorophenyl-amino)-2-dimethylamino-propane and 1-dimethylamino-2-(2,6-dichlorophenylamino)-propane

Method A

A mixture of 3.5 g (14.7 mmoles) of 1-(2,6-dichlorophenyl-amino)-2-chloro-propane, 35 ml of ethanol and 10 ml of a 33% aqueous dimethylamine solution is heated at 180° C. for 6 hours as described in Method (A) of Example 14 to obtain 1.9 g of a product, which is an about 15:85 mixture of the two title compounds. Yield: 52.3%; b.p.: 117°–118° C./93.3 Pa.

1.8 g of the above isomeric mixture are dissolved in 20 ml of ethyl acetate, 2.7 ml of a 11 w/v % isopropanolic hydrochloric acid solution are added, and the mixture is allowed to stand for some hours. 1.4 g of 1-dimethylamino-2(2,6-dichlorophenyl-amino)-propane hydrochloride separate from the mixture; m.p.: 173°–174° C.

The two isomers remained in the filtrate are separated from one another by chromatography as described in Method (A) of Example 14.

The starting substance, 1-(2,6-dichlorophenyl-amino)-2-propane, is prepared as follows:

STEP A

Preparation of 1-(2,6-dichlorophenyl-amino)-2-propanol hydrochloride 10 g (0.33 moles) of sodium hydride (a 85% dispersion in mineral oil) are added in small portions, at room temperature, to a solution of 60 g (0.32 moles) of 2,6-dichloroformanilide in 600 ml of dry dimethyl formamide. The mixture is heated to 90°–95° C., 45 ml (37.3 g, 0.64 moles) of 1,2-propylene-oxide are added dropwise to it within 2 hours, and the mixture is stirred for one additional hour at the same temperature. The mixture is cooled, poured onto 2 liters of ice water and extracted thrice with 300 ml of chloroform, each. The chloroform solutions are combined, washed thrice with 300 ml of water, each, dried over anhydrous magnesium sulfate, and the solvent is evaporated under reduced pressure. The oily residue, weighing 63.9 g, is dissolved in 100 ml of isopropanol, and a 11 w/v % isopropanolic hydrochloric acid solution (100 ml) is added. The mixture is allowed to stand overnight. Next day the separated crystalline product is filtered off, washed with isopropanol and dried. 48.7 g of the product are obtained. The mother liquor is concentrated, and the separated substance is filtered off. This fraction, weighing 13.35 g, is combined with the first fraction, and the product is recrystallized from 140 ml of isopropanol. 53.3 g (64.9%) of 1-(2,6-dichlorophenyl-amino)-2-propanol hydrochloride are obtained; m.p.: 135°–137° C.

STEP B

Preparation of
1-(2,6-dichlorophenyl-amino)-2-chloro-propane 3.4 ml (5.6 g, 47 mmoles) of thionyl chloride are added dropwise, within 0.5 hours, to a stirred suspension of 10 g (39 mmoles) of the salt obtained as described in Step (a) in 100 ml of dry benzene at room temperature. The mixture is boiled for 2 hours, then cooled to 50° C., and further 3.4 ml of thionyl chloride are added. The mixture is boiled again for one hour, thereafter further 3.4 ml of thionyl chloride are added, and boiling is continued for one hour. The mixture is cooled, 25 ml of water are added dropwise, and then the mixture is processed as described in Step (a) of Example 11. 7.3 g of 1-(2,6-dichlorophenyl-amino)-2-chloro-propane are obtained; b.p.: 118°–120° C./80 Pa.

METHOD B

A mixture of 5.0 g (16.8 mmoles) of 1-(2,6-dichlorophenyl-amino)-2-methanesulfonyloxy-propane, 50 ml of ethanol and 23 ml of a 33% aqueous dimethylamine solution is heated at 100° C. for 5 hours in a bomb. The reaction mixture is processed then as described in Method (A) of Example 14 to obtain 0.65 g (15.7%) of the product, which contains the two title compounds in a ratio of about 15:85, and 2.0 g 58.8%) of 1-(2,6-dichlorophenyl)-2-methyl-aziridine; b.p.: 92° C./93.3 Pa.

When 1-(2,6-dichlorophenyl)-2-methyl-aziridine is reacted with dimethylamine as described in Method (A) of Example 36, a mixture containing the two title compounds in a ratio of about 15:85 is obtained.

The starting substance, 1-(2,6-dichlorophenyl-amino)-2-methanesulfonyloxy-propane, is prepared as follows:

5.0 g (19.5 mmoles) of 1-(2,6-dichlorophenyl-amino)-2-propanol hydrochloride are added in small portions to 50 ml of dry pyridine, and then 3.1 ml (4.6 g, 40 mmoles) of methanesulfonyl chloride are added dropwise, within 0.5 hours, to the mixture at 15° C. The mixture is stirred at room temperature for one hour, then further 0.8 ml (1.2 g, 10 mmoles) of methanesulfonyl chloride are added, and stirring is continued for one hour. The mixture is poured then onto 100 ml of ice water, and the aqueous mixture is extracted thrice with 70 ml of 1,2-dichloroethane, each. The dichloroethane solutions are combined, washed thrice with 50 ml of water, each, dried over anhydrous magnesium sulfate, and the solvent is evaporated under reduced pressure. 5.52 g (79.5%) of 1-(2,6-dichlorophenyl-amino)-2-methanesulfonyloxy-propane are obtained as a dark yellow oil; this substance can be utilized in the subsequent reaction without purification.

EXAMPLE 37

Preparation of
1-(2,6-dimethylphenyl-amino)-2-(N-methyl-N-methoxycarbonyl)-amino-propane A solution of 0.46 ml (0.57 g, 6 mmoles) of methyl chloroformate in 10 ml of 1,2-dichloroethane is added dropwise, within 0.5 hours, to a solution of 1.05 g (5.2 mmoles) of 1-(2,6-dimethylphenyl-amino)-2-(methylamino)-propane and 0.81 ml (0.6 g, 5.7 mmoles) of triethylamine in 20 ml of 1,2-dichloroethane at 5°–10° C., and the mixture is stirred for additional 2 hours at the same temperature. The mixture is washed twice with 20 ml of water, each, the organic phase is dried over anhydrous magnesium sulfate, and the solvent is evaporated under reduced pressure. The oily residue is purified by chromatography on 40 g of silica gel; a 3:1 mixture of benzene and ethyl acetate is applied as eluant. 0.95 g (73.1%) of 1-(2,6-dimethylphenyl-amino)-2-(N-methyl-N-methoxycarbonyl)-amino-propane are obtained as an oily substance.

This product is converted into its hydrochloride as described in Example 1. The salt melts at 168°–170° C.

EXAMPLE 38

Preparation of
1-(2,6-dimethylphenyl-amino)-3-dimethylamino-butane

One proceeds as described in Example 1 with the difference that 1-[N-(2,6-dimethylphenyl)-methanesulfonamido]-3-dimethylamino-butane is applied as starting substance. The title compound, boiling at 122°–124° C./53.3 Pa, is obtained with a yield of 55.5%. The dihydrochloride monohydrate of the base melts at 115°–117° C.

The starting substance, 1-[N-(2,6-dimethylphenyl)-methanesulfonamido]-3-dimethylamino-butane, is prepared by reacting N-(2,6-dimethylphenyl)-methanesulfonamide with 1,3-dibromo-propane as described in Example 26, and treating the resulting crude 1-[N-(2,6-dimethylphenyl)-methanesulfonamido]-3-bromo-propane with aqueous dimethylamine as given in Example 30 for the preparation of the starting substance. The compound is obtained with a yield of 28.5%; its hydrochloride melts at 185°–186° C.

EXAMPLE 39

Preparation of
1-diisopropylamino-2-(2,6-dimethylphenyl-amino)-propane 1-(2,6-Dimethylphenyl-amino)-2-chloro-propane is reacted with diisopropylamine as described in Example 14 to obtain the crude title compound with a yield of 20.4%; b.p.: 124°–128° C./53.3 Pa. The crude base is converted into its hydrochloride as described in Example 1, and the salt is recrystallized from a 1:10 mixture of isopropanol and ethyl acetate to obtain the pure dihydrochloride monohydrate melting at 165°–167° C.

EXAMPLE 40

Preparation of
1-[N-(2,6-dimethylphenyl)-N-(ethoxycarbonyl)-amino]-2-dimethylamino-propane 0.78 ml (0.88 g, 8 mmoles) of ethyl chloroformate are added to a mixture of 1.0 g (4.85 mmoles) of 1-(2,6-dimethylphenyl-amino)-2-dimethylamino-propane, prepared as described in Example 8, 0.60 ml (0.51 g, 5 mmoles) of triethylamine and 20 ml of 1,2-dichloroethane, and the reaction mixture is boiled for 6 hours. The mixture is washed thrice with 10 ml of water, each, dried over anhydrous magnesium sulfate, and the solvent is evaporated under reduced pressure. The oily residue is subjected to column chromatography on 20 g of silica gel, applying ethyl acetate as eluant. 0.91 g (67.4%) of 1-[N-(2,6-dimethylphenyl)-N-ethoxycarbonyl-amino]-2-dimethylamino-propane are obtained as a light yellow, oily substance. The hydrochloride of this base melts at 165°–167° C.

EXAMPLE 41

Preparation of
1-[N-methyl-N-(2,6-dimethylphenyl)-amino]-2-dimethylamino-propane A mixture of 1.5 g (7.3 mmoles) of 1-(2,6-dimethylphenyl-amino)-2-dimethylamino-propane, prepared as described in Example 8, 1.5 ml of 99% formic acid and 1.5 ml of a 36% aqueous formaldehyde solution is boiled for 6 hours. The mixture is cooled, poured onto 30 ml of water, the aqueous solution is rendered alkaline (pH=9) with concentrated aqueous ammonia, and extracted then thrice with 10 ml of benzene, each. The benzene solutions are combined, dried over anhydrous potassium carbonate, and the solvent is evaporated under reduced pressure. 1.58 g (98,8%) of 1-[N-methyl-N-(2,6-dimethylphenyl)-amino]2-dimethylamino-propane are obtained as a light yellow oil; b.p.: 102°–104° C./133.3 Pa.

EXAMPLE 42

Preparation of
1-[N-(2,6-dimethylphenyl)-acetamido]-2-dimethylamino-propane

A mixture of 3.0 g (12.5 mmoles) of 1-[N-(2,6-dimethylphenyl)-acetamido]-2-chloro-propane and 9.4 ml of a 18 w/v % ethanolic dimethylamine solution is heated at 60° C. for 3 hours in a bomb. The mixture is cooled, admixed with 50 ml of benzene and 10 ml of water, and the organic phase is separated. The aqueous phase is extracted twice with 10 ml of benzene, each. The benzene solutions are combined, dried over anhydrous magnesium sulfate, and the solvent is evaporated under reduced pressure. 2.8 g (90.3%) of 1-[N-(2,6-dimethylphenyl)-acetamido]-2dimethylamino-propane are obtained as a thick, light yellow oil; b.p.: 140°–141° C./120 Pa. The hydrochloride monohydrate of the base melts at 170°–172° C.

The reaction can also be performed so that the mixture is stirred at room temperature for 48 hours.

By removing the acetyl group of the product a compound identical with the product of Example 8 is obtained.

The starting substance, 1-[N-(2,6-dimethylphenyl)-acetamido]-2-chloro-propane, is prepared as follows:

STEP A

Preparation of
1-[N-(2,6-dimethylphenyl)-acetamido]-2-propanol

A mixture of 20.5 g (0.144 moles) of 1-(2,6-dimethylphenl-amino)-2-propanol and 60 ml of acetic anhydride is stirred at room temperature for 2 hours, and then the excess of acetic anhydride is evaporated under reduced pressure. The oily residue is added to a solution of 15 g of sodium hydroxide in 150 ml of ethanol, the mixture is stirred at room temperature for 2 hours, and then poured onto 500 ml of ice water. The aqueous solution is extracted thrice with 100 ml of chloroform, each. The chloroform solutions are combined, washed thrice with 100 ml of water, each, dried over anhydrous magnesium sulfate, and the solvent is evaporated under reduced pressure. 24.7 g (97.6%) of 1-[N-(2,6-dimethylphenyl)-acetamido]-2-propanol are obtained; m.p.: 64°–67° C.

STEP B

Preparation of
1-[N-(2,6-dimethylphenyl)-acetamido]-2-chloro-propane 6.5 ml (10.76 g, 90.4 mmoles) of thionyl chloride are added dropwise, within 20 minutes, to a solution of 20 g (90.4 mmoles) of 1[N-(2,6-dimethylphenyl)-acetamido]-2-propanol in 200 ml of benzene, and the mixture is boiled until the gas evolution ceases (for about 0.25 hours). The mixture is cooled, the solvent is evaporated under reduced pressure, and the oily residue is distilled under reduced pressure. 17.75 g (81.9%) of 1-[N-(2,6-dimethylphenyl)-acetamido]-2-chloro-propane are obtained; b.p.: 138°–140° C./93.3 Pa, m.p.: 41°–42° C.

EXAMPLE 43

Preparation of
1-[N-(2,6-dimethylphenyl)-trifluoro-acetamido]-2-dimethylamino-propane A mixture of 1.0 g (4.8 mmoles) of 1-(2,6-dimethylphenyl-amino)-2-dimethylamino-propane, prepared as described in Example 8, and 5 ml of trifluoroacetic anhydride is allowed to stand at room temperature for 5 hours, and then the excess of trifluoroacetic anhydride is evaporated under reduced pressure. The oily residue is dissolved in 30 ml of water, the solution is rendered alkaline (pH=9) with concentrated aqueous ammonia, and extracted thrice with 10 ml of chloroform, each. The chloroform solutions are combined, washed twice with 10 ml of water, each, dried over anhydrous magnesium sulfate, and the solvent is evaporated under reduced pressure. The resulting oily substance, weighing 1.25 g, is dissolved in 2 ml of a 10 w/v % ethanolic hydrochloric acid solution, and the product is precipitated with 40 ml of dry diethyl ether. The separated shiny, crystalline substance is filtered off, washed with diethyl ether and dried. 1.2 g (74%) of 1-[N-(2,6-dimethylphenyl)-trifluoroacetamido]-2-dimethylamino-propane hydrochloride are obtained; m.p.: 150°–153° C.

EXAMPLES 44 TO 46

The compounds listed below are prepared by using the appropiate amines, compounds according to the method of Example 16.

EXAMPLE 44

1-[N-(2,6-dimethylphenyl)-methanesulfonamido]-2-(1,4-oxazin-4-yl)-propane; yield: 83%, m.p.: 127°–128° C.

EXAMPLE 45

1-[N-(2,6-dimethylphenyl)-methanesulfonamido]-2-(piperidine-1-yl)-propane; yield: 54%, m.p.: 83°–84° C.

EXAMPLE 46

1-[N-(2,6-dimethylphenyl)-methanesulfonamido]-2-(2-hydroxy-ethylamino)-propane; yield: 77%, m.p.: 82°–84° C.

EXAMPLES 47 TO 49

The products prepared according to Examples 44 to 46 are subjected to the treatment described in Example 1 to obtain the following compounds:

EXAMPLE 47

1-(2,6-dimethylphenyl-amino)-2-(1,4-oxazin-4-yl)-propane; yield: 73%, b.p.: 140°–144° C./26.6 Pa, the dihydrochloride melts at 170°–175° C.

EXAMPLE 48

1-(2,6-dimethylphenyl-amino)-2-(piperidin-1-yl)-propane; yield: 73%, b.p.: 138°–140° C./93.3 Pa, the dihydrochloride melts at 170°–174° C.

EXAMPLE 49

1-(2,6-dimethylphenyl-amino)-2-(2-hydroxy-ethylamino)-propane; yield: 87%, b.p.: 186° C./186.6 Pa, the dihydrochloride melts at 163°–168° C.

EXAMPLE 50

Preparation of 1-(2,6-dimethylphenyl-amino)-22-chloro-ethylamino)-propane 4 ml of thionyl chloride are added to a suspension of 10.0 g (35.1 mmoles) of 1-(2,6-dimethylphenyl-amino)-2-(2hydroxyethylamino)-propane dihydrochloride, prepared as des ribed in Example 49, in 100 ml of dry toluene, and the mixture is stirred at 80° C. for 3 hours and then at 100° C. for one hour. The mixture is cooled, the separated precipitate is filtered off, washed with toluene and dried. 10.1 g (92%) of 1-(2,6-dimethylphenyl-amino)-2-(2-chloro-ethylamino)-propane dihydrochloride are obtained; m.p.: 163°–168° C.

EXAMPLE 51

Preparation of 1-(2,6-dimethylphenyl-amino)-2-(aziridin-1-yl)-propane

One proceeds as described in Example 1 with the difference that 1-[N-(2,6-dimethylphenyl)-methanesulfonamido]-2-(aziridin-1-yl)-propane is applied as starting substance. The title compound is obtained with a yield of 26%; b.p.: 94° C./13.3 Pa.

The starting substance, 1-[N-(2,6-dimethylphenyl)-methanesulfonamido]-2-(aziridin-1-yl)-propane, is prepared as follows:

STEP A

Preparation of 1-[N-(2,6-dimethylphenyl)-methanesulfonamido]-2(2-chloro-ethylamino)-propane The title compound is prepared as described in Example 50, with the difference that 1-[N-(2,6-dimethylphenyl)-methane-sulfonamido]-2-(2-hydroxy-ethylamino)-propane, prepared according to Example 46, is applied as starting substance. The product is obtained with a yield of 87%; its hydrochloride melts at 185°–190° C.

STEP B

Preparation of 1-[N-(2,6-dimethylphenyl)-methanesulfonamido]-2-(aziridin-1-yl)-propane 5.0 g (14 mmoles) of 1-[N-(2,6-dimethylphenyl)-methanesulfonamido]-2-(2-chloro-ethylamino)-propane, prepared as described in Step (a) above, are added to a mixture of 100 ml of ethanol and 10 ml of a 10 n aqueous sodium hydroxide solution, and the reaction mixture is stirred and boiled for one hour. The mixture is cooled, poured onto 300 ml of water, and extracted thrice with 50 ml of chloroform, each. The chloroform solutions are combined, washed thrice with 20 ml of water, each, dried over magnesium sulfate, and the solvent is evaporated. 3.9 g (98%) of 1-[N-(2,6-dimethylphenyl)-methanesulfonamido]-2-(arixidin-1-yl)-propane are obtained as a thick, colourless oil.

EXAMPLE 52

Preparation of 1-(2,6-dimethylphenyl-amino)-2-(2-diethylamino-acetamido)-propane A solution of 2.8 g of diethylamino-acetyl chloride hydrochloride in 10 ml of dry chloroform is added dropwise, within 20 minutes, to a mixture of 2.25 g (12.7 mmoles) of 1-(2,6-dimethylphenyl-amino)-2-amino-propane, prepared as described in Example 1, 4.2 ml (3.08 g, 30 mmoles) of triethylamine and 20 ml of dry chloroform at 5°–10° C., and the resulting mixture is stirred at room temperature for one hour. Thereafter a solution of 20 mmoles of dry hydrochloric acid in 10 ml of isopropanol is added, and the solvent is evaporated under reduced pressure.

The oily residue is dissolved in a two-phase mixture of 80 ml of benzene and 10 ml of water, the mixture is rendered alkaline with an 5 n aqueous sodium hydroxide solution, and the benzene phase is separated. The aqueous phase is extracted twice with 10 ml of benzene, each. The benzene solutions are combined, dried over anhydrous magnesium sulfate, and the solvent is evaporated under reduced pressure. The oily residue is subjected to column chromatography on silica gel, applying a 6:1 mixture of benzene and pyridine as eluant. The fractions which contain the required product are combined, the solvent is evaporated under reduced pressure, and the resulting oily product is converted into the dihydrochloride as described in Example 1. The colourless, hygroscopic, crystalline salt, melting at 75°–80° C., is obtained with a yield of 21%.

EXAMPLE 53

Preparation of 1-(2,6-dimethylphenyl-amino)-3-amino-butane

One proceeds as described in Example 1 with the difference that 1-[N-(2,6-dimethylphenyl)-methanesulfonamido]-3-amino-butane is applied as starting substance. The title compound is obtained with a yield of 84%; b.p.: 136°–138° C./133.3 Pa. The dihydrochloride of the product melts at 225°–227° C.

This compound is identical with the major component of the isomeric mixture obtained according to Example 7.

The starting substance, 1-[N-(2,6-dimethylphenyl)-methanesulfonamido]-2-amino-butane, is prepared as follows:

STEP A

Preparation of 1-[N-(2,6-dimethylphenyl)-methanesulfonamido]-3-bromo-butane 15.5 g (0.517 moles) of a 80% sodium hydride dispersion, containing 20% of mineral oil, are added in small portions, within 0.5 hours, to a suspension of 100 g (0.5 moles) of N-(2,6-dimethylphenyl)-methanesulfonamide in 800 ml of dry xylene at room temperature, and the mixture is heated then to 130° C. within one hour. 102.5 ml (184.5 g, 0.85 moles) of 1,3-dibromo-butane are added dropwise, within 3 hours, to the mixture at 130°–135° C., and the mixture is stirred at the same temperature for additional 4 hours. Thereafter the mixture is cooled, washed twice with 200 ml of water, twice with 250 ml of 1 n aqueous sodium hydroxide solution, once with 200 ml of water, twice with 200 ml of 1 n aqueous hydrochloric acid solution and finally twice with 200 ml of water, each, dried over anhydrous magnesium sulfate, and the solvent is evaporated under reduced pressure. 109.65 g (66%) of crude 1-[N-(2,6-dimethylphenyl)-methanesulfonamido]-3-bromo-butane are obtained as a dark yellow oil; this substance can be utilized in the next step without purification.

The crude product crystallizes upon standing for several days. The crystals melt at 66°–68° C. after recrystallization from isopropanol.

STEP B

Preparation of 1-[N-(2,6-dimethylphenyl)-methane-sulfonamido]-3phthalimido-butane The intermediate obtained as described in Step (a) above is reacted with potassium phthalimide as described in paragraph 2 of Example 26. Pure 1-[N-(2,6-dimethylphenyl)-methanesulfonamido]-3-phthalimido-butane, melting at 148°–152° C., is obtained with a yield of 58%. This compound is identical with the major component of the isomeric mixture prepared according to Example 26.

STEP C

Preparation of 1-[N-(2,6-dimethylphenyl)-methane-sulfonamido]-3-amino-butane The intermediate obtained as described in Step (b) above is treated with hydrazine as described in Example 23 to obtain pure 1-[N-(2,6-dimethylphenyl)-methanesulfonamido]-3-amino-butane with a yield of 99%. The hydrochloride of the product melts at 218°–220° C. with decomposition. The product is identical with the major component of the isomeric mixture prepared according to Example 23.

EXAMPLE 54

Preparation of 1-[N-methyl-N-(2,6-dimethylphenyl)-amino]-2-dimethylamino-propane N-oxide 7.5 ml of a 30% aqueous hydrogen peroxide solution are added dropwise, under coolig with water, to a solution of 2.2 g (10 mmoles) of 1-[N-methyl-N-(2,6-dimethylphenyl)-amino]-2-dimethylamino-propane in 2.5 ml of acetic anhydride, and the mixture is heated then on a steam bath for 3 hours. The mixture is cooled, the solvent is evaporated under reduced pressure, the oily residue is dissolved in 30 ml of water, the solution is rendered alkaline with a 5 n aqueous sodium hydroxide solution, and the mixture is shaken thrice with 10 ml of diethyl ether, each, in order to remove the unreacted starting substance. Thereafter the aqueous phase is extracted five times with 30 ml of chloroform, each, the chloroform solutions are combined, dried over anhydrous magnesium sulfate, and the solvent is evaporated under reduced pressure. 0.45 g (40%, calculated for the converted starting substance) of 1-[N-methyl-N-(2,6-dimethylphenyl)-amino]-2-dimethylamino-propane N-oxide are obtained as a yellow oil.

EXAMPLE 55

Preparation of tablets

Composition of one tablet:

| | |
|---|---:|
| 1-(2,6-Dimethylphenyl-amino)-2-dimethylamino-propane dihydrochloride | 150 mg |
|  | 150 |
| Elcema P 100* | 50 mg |
| Elcema G 250* | 240 mg |
| Talc | 7 mg |
| Magnesium stearate | 3 mg |
| Total: | 450 mg |

*Microcrystalline cellulose, produced by the firm Degussa, German Federal Republic.

The individual components are admixed with each other in the given order, the mixture is homogenized, and then compressed directly into tablets. The strength of the tablet is 5.5 kg.

EXAMPLE 56

Preparation of Injectable Solutions

Composition of one ampoulle:

| | |
|---|---:|
| 1-(2,6-Dimethylphenyl-amino)-2-dimethylamino-propane dihydrochloride | 150 mg |
|  | 150 |
| Sodium chloride | 20 mg |
| Water for injection purposes q.s. ad | 2 ml |

What is claimed is:

1. 1-(2,6-Dimethylphenyl-amino)-2-dimethylaminopropane dihydrochloride.

2. A pharmaceutical composition for treating cardiac rhythm disorders which comprises:
   a pharmaceutically acceptable carrier and/or diluent and an effective amount of the compound 1-(2,6-dimethylphenyl-amino)-2-dimethylaminopropane dihydrochloride.

* * * * *

UNITED STATES PATENT AND TRADEMARK OFFICE
CERTIFICATE OF CORRECTION

PATENT NO. : 4,922,021

DATED : May 1, 1990

INVENTOR(S) : Zoltan ZUBOVICS et al.

It is certified that error appears in the above-identified patent and that said Letters Patent is hereby corrected as shown below:

On the title page:

Named assignee "BASF Aktiensellschaft, Ludwigshafen, Fed. Rep. of Germany" should read --ALKALOIDA Vegyeszeti Gyar, Tiszavasvari, Hungary--

Signed and Sealed this

Fourth Day of June, 1991

Attest:

HARRY F. MANBECK, JR.

Attesting Officer

Commissioner of Patents and Trademarks